United States Patent
Fischer et al.

(10) Patent No.: US 11,401,299 B2
(45) Date of Patent: Aug. 2, 2022

(54) GENERATING MULTISPECIFIC ANTIBODY MIXTURES AND METHODS OF USES THEREOF

(71) Applicant: NovImmune SA, Geneva (CH)

(72) Inventors: Nicolas Fischer, Geneva (CH); Giovanni Magistrelli, Cessy (FR); Krzysztof Masternak, Mollens (CH)

(73) Assignee: NovImmune SA, Geneva (CH)

( * ) Notice: Subject to any disclaimer, the term of this patent is extended or adjusted under 35 U.S.C. 154(b) by 236 days.

(21) Appl. No.: 16/042,889

(22) Filed: Jul. 23, 2018

(65) Prior Publication Data

US 2019/0031714 A1    Jan. 31, 2019

Related U.S. Application Data

(60) Provisional application No. 62/535,354, filed on Jul. 21, 2017.

(51) Int. Cl.

| | |
|---|---|
| *C07K 1/22* | (2006.01) |
| *C07K 16/06* | (2006.01) |
| *C07K 16/46* | (2006.01) |
| *A61K 39/00* | (2006.01) |
| *A61P 35/00* | (2006.01) |
| *C07K 16/30* | (2006.01) |
| *C07K 16/00* | (2006.01) |
| *C07K 16/28* | (2006.01) |

(52) U.S. Cl.
CPC ............... *C07K 1/22* (2013.01); *A61P 35/00* (2018.01); *C07K 16/00* (2013.01); *C07K 16/065* (2013.01); *C07K 16/2803* (2013.01); *C07K 16/30* (2013.01); *C07K 16/468* (2013.01); *A61K 2039/505* (2013.01); *A61K 2039/507* (2013.01); *C07K 2317/10* (2013.01); *C07K 2317/21* (2013.01); *C07K 2317/31* (2013.01); *C07K 2317/51* (2013.01); *C07K 2317/73* (2013.01); *C07K 2317/92* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,926,382 | B2 * | 3/2018 | Fischer | C12N 15/1075 |
| 10,047,144 | B2 * | 8/2018 | Elson | C07K 16/00 |
| 10,457,749 | B2 * | 10/2019 | Fouque | C07K 1/20 |
| 10,597,465 | B2 * | 3/2020 | Fischer | C07K 16/248 |
| 2012/0184716 | A1 | 7/2012 | Fischer et al. | |
| 2013/0317200 | A1 * | 11/2013 | Elson | C07K 16/2866 |
| | | | | 530/387.3 |
| 2014/0179547 | A1 | 6/2014 | Fischer et al. | |
| 2016/0264685 | A1 | 9/2016 | Fouque et al. | |

FOREIGN PATENT DOCUMENTS

| | | |
|---|---|---|
| RU | 2625034 C2 | 7/2017 |
| WO | WO 2008/106200 A2 | 9/2008 |
| WO | WO 2012/023053 A2 | 2/2012 |
| WO | WO 2013/088259 A2 | 6/2013 |
| WO | WO 2014/087248 A2 | 6/2014 |
| WO | WO2015024896 A1 | 2/2015 |

OTHER PUBLICATIONS

Rouet "Bispecific antibodies with native chain structure" Nature Biotechnology, Feb. 2014, 32(2) (Year: 2014).*
Gagnon et al. "Minibodies and Multimodal Chromatography Methods: A convergence of challenge and opportunity" Bioprocess Int. Feb. 2010; 8(2): 26-35 (Year: 2010).*
Arena et al. (Feb. 3, 2016), "MM-151 overcomes acquired resistance to cetuximab and panitumumab in colorectal cancers harboring EGFR extracellular domain mutations" *Science Translational Medicine*, 8(324): 324ra14, 11 pages.
Brinkmann, U. and R.E. Kontermann (2017) "The making of bispecific antibodies" *mAbs*, 9:182-212.
Chames, P. and D. Baty (2009) "Bispecific antibodies for cancer therapy" *mAbs*, 1(6):539-547.
Fischer, N. (2008) "New magic bullets can hit more than one targe" *Expert Opin Drug Discov*, 3(8):833-839.
Fischer, N. and O. Léger (2007) "Bispecific antibodies: Molecules That Enable Novel Therepeutic Strategies" *Pathology*, 74(1):3-14.
Fischer, N. et al. (Feb. 12, 2015) "Exploiting light chains for the scalable generation and platform purification of native human bispecific IgG" *Nature Communications*, 6:6113; doi: 10.1038/ncomms7113, 12 pages.
Harris, S.J. et al. (2016) "Immuno-oncology combinations: raising the tail of the survivial curve" *Cancer Biol Med*, 13(2):171-193.
Hjelmström, P. et al. (2008) "Sym001, the First Recombinant Polyclonal Rhesus-D Specific Antibody Product, Was Safe and Well-Tolerated in a Placebo-Controlled Randomized Phase I Trial" *Blood*, 112:1987, 2 pages.
Koefoed, K. et al. (2011) "Rational identification of an optimal antibody mixture for targeting the epidermal growth factor receptor" *mAbs*, 3(6):584-595.

(Continued)

*Primary Examiner* — Daniel E Kolker
*Assistant Examiner* — James L Rogers
(74) *Attorney, Agent, or Firm* — Cooley LLP; Ivor R. Elrifi; Cynthia A. Kozakiewicz

(57) ABSTRACT

The invention relates to the generation of multispecific antibody mixtures include a subset of antibodies isolated from a mixture of two or more monospecific antibodies and one or more bispecific antibodies, wherein all antibodies in the subset have the same common heavy chain. The invention also relates to methods of isolating, purifying, or otherwise producing such a subset of antibodies by using at least one affinity chromatography step. The invention also relates to methods of using such a subset of antibodies in a variety of therapeutic indications.

3 Claims, 18 Drawing Sheets

Specification includes a Sequence Listing.

(56) References Cited

OTHER PUBLICATIONS

Larkin, J. et al. (2015) "Combined Nivolumab and Ipilimumab or Monotherapy in Untreated Melanoma" *N Engl J Med*, 373:23-34.
Oldenborg, P-A. (2013) "CD47: A Cell Surface Glycoprotein Which Regulates Multiple Functions of Hematopoietic Cells in Health and Disease" *ISRN Hematol*, 2013:614619, 19 pages.
Oleksiewicz, M.B. et al. (2012) "Anti-bacterial monoclonal antibodies: Back to the future?" *Archives of Biochemistry and Biophysics*, 526:124-131.
Pohl, M.A. et al. (2013) "Combinations of Monoclonal Antibodies to Anthrax Toxin Manifest New Properties in Neutralizaiton Assays" *Infection and Immunity*, 81(6):1880-1888.
Raju, T.S. and W.R. Strohl (2013) "Potential therapeutic roles for antibody mixtures" *Expert Opin Biol Ther* 13(10):1347-1352.
Rasmussen, S.K. et al. (2012) "Recombinant antibody mixtures: Production strategies and cost considerations" *Archives of Biochemistry and Biophysics*, 526:139-145.
Robak, T. et al. (2012) "Rozrolimupab, a mixture of 25 recombinant human monoclonal RhD antibodies, in the treatment of primary immune thrombocytopenia" *Blood*, 120(18):3670-3676.
Sick, E. et al. (Dec. 2012) "CD47 update: a multifaced actor in the tumor microenvironment of potential therapeutic interest" *Br J Pharmacol*, 167(7):1415-1430.
Soto-Pantoja, D.R. et al. (Jan. 2013) "Therapeutic opportunities for targeting the ubiquitous cell surface receptor CD47" *Expert Opin Ther Targets*, 17(1):89-103.
Spiess, C. et al. (2015) "Alternative molecular formats and therapeutic applications for bispecific antibodies" *Mol Immunol*, 67:95-106.
Wang, X-z. et al. (2013) "Back to the future: recombinant polyclonal antibody therapeutics" *Current Opinion in Chemical Engineering*, 2:405-415.
Tarantul, V.Z., "Russian-English Explanatory Biotechnological Dictionary," Languages of Slavic Cultures, Moscow, 2009, pp. 87.
Office Action for Russian Application No. RU202001073111 dated Apr. 22, 2022, 15 pages.

* cited by examiner

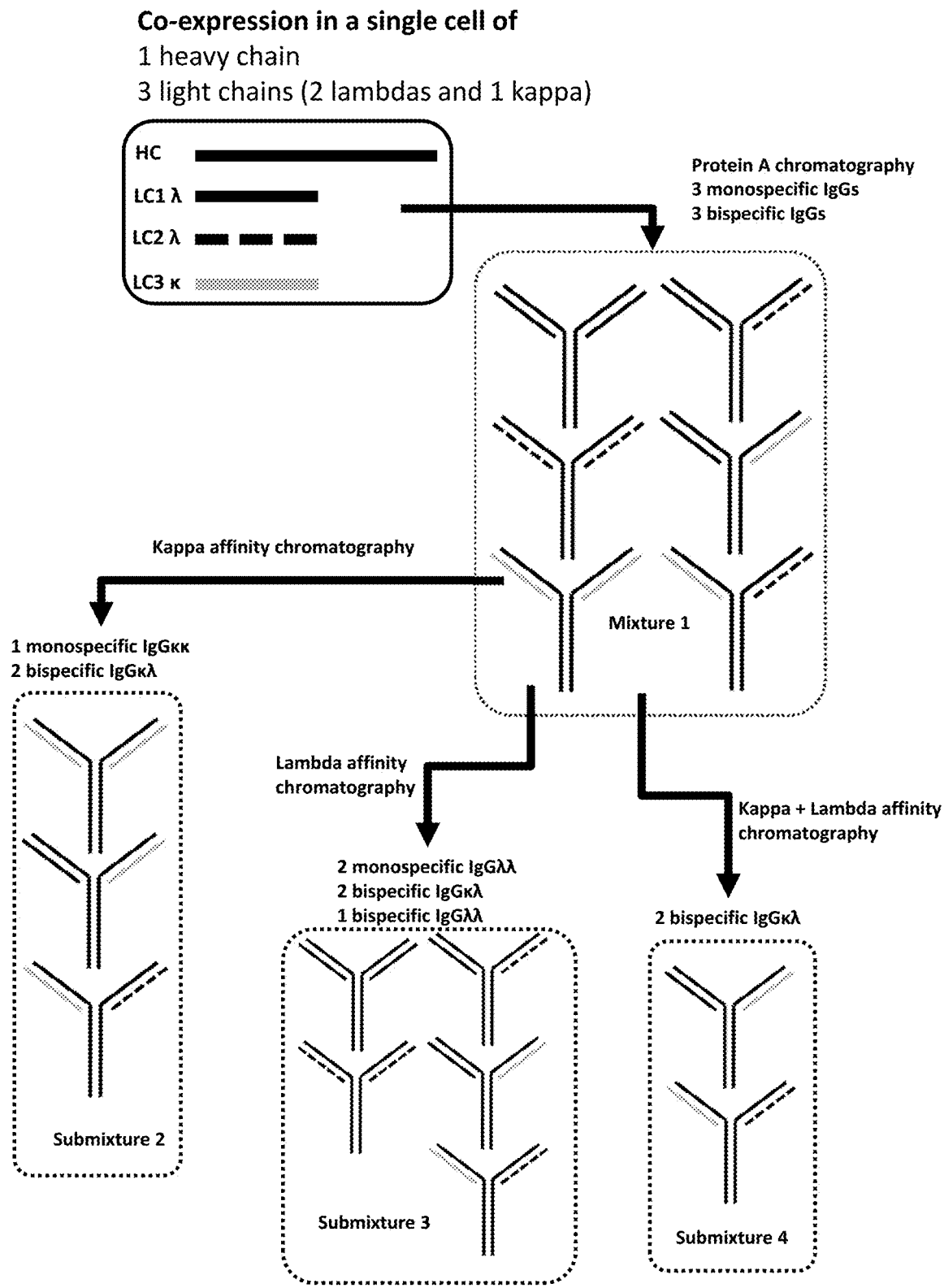

SEQUENCE LISTING

<160> NUMBER OF SEQ ID NOS: 32

<210> SEQ ID NO 1
<211> LENGTH: 1338
<212> TYPE: DNA
<213> ORGANISM: Artificial Sequence
<220> FEATURE:
<223> OTHER INFORMATION: Synthetic Polynucleotide

<400> SEQUENCE: 1

```
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagttat     300
ggtgcttttg actactgggg ccaggaaacc ctggtcacag tctcgagcgc ctccaccaag     360
ggcccatcgg tcttccccct ggcaccctcc tccaagagca cctctggggg cacagcggcc     420
ctgggctgcc tggtcaagga ctacttcccc gaaccggtga cagtctcgtg gaactcagga     480
gccctgacca gcggcgtgca caccttcccg gctgtcctac agtcctcagg actctactcc     540
ctcagcagcg tggtgactgt gccctccagc agcttgggca cccagaccta catctgcaac     600
gtgaatcaca agcccagcaa caccaaggtg gacaagagag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatctc gggaggagat gaccaagaac    1080
caggtcagcc tgacttgcct ggtcaaaggc ttctatccca gcgacatcgc cgtggagtgg    1140
gagagcaacg ggcagccgga gaacaactac aagaccacgc ctcccgtgct ggactccgac    1200
ggctccttct tcctctatag caagctcacc gtggacaagt ccaggtggca gcaggggaac    1260
gtcttctcat gctccgtgat gcatgaggct ctgcacaacc actacacgca gaagagcctc    1320
tccctgtctc cgggttaa                                                 1338
```

<210> SEQ ID NO 2

<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly
        435                 440                 445

<210> SEQ ID NO 3
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 3
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtat attactgtgc gaaaagttat     300
ggtgcttttg actactgggg ccagggaacc ctggtcacag tctcgagc                  348

<210> SEQ ID NO 4
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115

<210> SEQ ID NO 5
<211> LENGTH: 675
<212> TYPE: DNA
<213> ORGANISM: Artificial Sequence
<220> FEATURE:
<223> OTHER INFORMATION: Synthetic Polynucleotide

<400> SEQUENCE: 5

```
cagcctgtgc tgactcagcc ggcttccctc tctgcatctc ctggagcatc agccagtctc    60
acctgcacct tgcacagtgg catctctgtt aaggattaca ggatatactg gtaccagcag   120
aagccagggc gtcctcccca gtatctcctg aggtacaagt ctaattcaga tatgcagcag   180
ggatctggag tccccagccg cttctctggg tccaaagatg cttcggccaa tgcagggatt   240
ttactcatct ctgggctcca gtctgaggat gaggctgact attactgtat gatttggcac   300
catggccatg gactagtctg tgtgttcggc ggagggacca agctgaccgt cctaggtcag   360
cccaaggctg cccctcggt cactctgttc ccgccctcct ctgaggagct tcaagccaac   420
aaggccacac tggtgtgtct cataagtgac ttctacccgg gagccgtgac agtggcttgg   480
aaagcagata gcagccccgt caaggcggga gtggagacca ccacccctc caaacaaagc   540 aacaacaagt acgcggccag cagctatctg agcctgacgc ctgagcagtg gaagtcccac   600
agaagctaca gctgccaggt cacgcatgaa gggagcaccg tggagaagac agtggcccct   660
acagaatgtt cataa                                                    675
```

<210> SEQ ID NO 6
<211> LENGTH: 224
<212> TYPE: PRT
<213> ORGANISM: Artificial Sequence
<220> FEATURE:
<223> OTHER INFORMATION: Synthetic Polypeptide

<400> SEQUENCE: 6

```
Gln Pro Val Leu Thr Gln Pro Ala Ser Leu Ser Ala Ser Pro Gly Ala
1               5                   10                  15

Ser Ala Ser Leu Thr Cys Thr Leu His Ser Gly Ile Ser Val Lys Asp
            20                  25                  30

Tyr Arg Ile Tyr Trp Tyr Gln Gln Lys Pro Gly Arg Pro Pro Gln Tyr
        35                  40                  45

Leu Leu Arg Tyr Lys Ser Asn Ser Asp Met Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His His Gly His Gly Thr Ser Leu Val Phe Gly Gly Gly
            100                 105                 110

Thr Lys Leu Thr Val Leu Gly Gln Pro Lys Ala Ala Pro Ser Val Thr
        115                 120                 125

Leu Phe Pro Pro Ser Ser Glu Glu Leu Gln Ala Asn Lys Ala Thr Leu
    130                 135                 140

Val Cys Leu Ile Ser Asp Phe Tyr Pro Gly Ala Val Thr Val Ala Trp
145                 150                 155                 160

Lys Ala Asp Ser Ser Pro Val Lys Ala Gly Val Glu Thr Thr Thr Pro
                165                 170                 175

Ser Lys Gln Ser Asn Asn Lys Tyr Ala Ala Ser Ser Tyr Leu Ser Leu
            180                 185                 190

Thr Pro Glu Gln Trp Lys Ser His Arg Ser Tyr Ser Cys Gln Val Thr
        195                 200                 205

His Glu Gly Ser Thr Val Glu Lys Thr Val Ala Pro Thr Glu Cys Ser
    210                 215                 220
```

<210> SEQ ID NO 7
<211> LENGTH: 354

<210> SEQ ID NO 7
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 7

```
cagcctgtgc tgactcagcc ggcttccctc tctgcatctc ctggagcatc agccagtctc    60
acctgcacct tgcacagtgg catctctgtt aaggattaca ggatatactg gtaccagcag   120
aagccagggc gtcctcccca gtatctcctg aggtacaagt ctaattcaga tatgcagcag   180
ggatctggag tccccagccg cttctctggg tccaaagatg cttcggccaa tgcagggatt   240
ttactcatct ctgggctcca gtctgaggat gaggctgact attactgtat gatttggcac   300
catggccatg gactagtct tgtgttcggc ggagggacca agctgaccgt ccta            354
```

<210> SEQ ID NO 8
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 8

```
Gln Pro Val Leu Thr Gln Pro Ala Ser Leu Ser Ala Ser Pro Gly Ala
1               5                   10                  15
Ser Ala Ser Leu Thr Cys Thr Leu His Ser Gly Ile Ser Val Lys Asp
            20                  25                  30
Tyr Arg Ile Tyr Trp Tyr Gln Gln Lys Pro Gly Arg Pro Pro Gln Tyr
        35                  40                  45
Leu Leu Arg Tyr Lys Ser Asn Ser Asp Met Gln Gln Gly Ser Gly Val
    50                  55                  60
Pro Ser Arg Phe Ser Gly Ser Lys Asp Ala Ser Ala Asn Ala Gly Ile
65                  70                  75                  80
Leu Leu Ile Ser Gly Leu Gln Ser Glu Asp Glu Ala Asp Tyr Tyr Cys
                85                  90                  95
Met Ile Trp His His Gly His Gly Thr Ser Leu Val Phe Gly Gly Gly
            100                 105                 110
Thr Lys Leu Thr Val Leu
        115
```

<210> SEQ ID NO 9
<211> LENGTH: 657
<212> TYPE: DNA
<213> ORGANISM: Artificial Sequence
<220> FEATURE:
<223> OTHER INFORMATION: Synthetic Polynucleotide

<400> SEQUENCE: 9

```
cagtctgtgc tgactcagcc accctcagcg tctgggaccc ccgggcagag ggtcaccatc    60
tcttgttctg gaagcagctc caacatcgcg catgggcctg taaactggta ccagcagctc   120
ccaggaacgg cccccaaact cctcatctat gctactaatc atcggccctc aggggtccct   180
gaccgatttt ctggctccaa gtctggcacc acagcctccc tgaccatcag tgggctccag   240
tctgaggatg aggctgatta ttactgtgct gcatatgatc ttacgggctg gtttgcgtat   300
gctgtgttcg gcggagggac caagctgacc gtcctaggtc agcccaaggc tgccccctcg   360
gtcactctgt tcccgccctc ctctgaggag cttcaagcca acaaggccac actggtgtgt   420
ctcataagtg acttctaccc gggagccgtg acagtggctt ggaaagcaga tagcagcccc   480
```

```
gtcaaggcgg gagtggagac caccacaccc tccaaacaaa gcaacaacaa gtacgcggcc      540
agcagctatc tgagcctgac gcctgagcag tggaagtccc acagaagcta cagctgccag      600
gtcacgcatg aagggagcac cgtggagaag acagtggccc tacagaatg ttcataa          657
```

```
<210> SEQ ID NO 10
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 10
```

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Ala His Gly
            20                  25                  30

Pro Val Asn Trp Tyr Gln Gln Leu Pro Gly Thr Ala Pro Lys Leu Leu
        35                  40                  45

Ile Tyr Ala Thr Asn His Arg Pro Ser Gly Val Pro Asp Arg Phe Ser
    50                  55                  60

Gly Ser Lys Ser Gly Thr Thr Ala Ser Leu Thr Ile Ser Gly Leu Gln
65                  70                  75                  80

Ser Glu Asp Glu Ala Asp Tyr Tyr Cys Ala Ala Tyr Asp Leu Thr Gly
                85                  90                  95

Trp Phe Ala Tyr Ala Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

```
<210> SEQ ID NO 11
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 11
cagtctgtgc tgactcagcc accctcagcg tctgggaccc ccgggcagag ggtcaccatc      60
tcttgttctg gaagcagctc caacatcgcg catgggcctg taaactgta ccagcagctc      120 ccaggaacgg cccccaaact cctcatctat gctactaatc atcggccctc agggggtccct    180 gaccgatttt ctggctccaa gtctggcacc acagcctccc tgaccatcag tgggctccag    240
tctgaggatg aggctgatta ttactgtgct gcatatgatc ttacgggctg gtttgcgtat    300
gctgtgttcg gcggagggac caagctgacc gtccta                               336
```

<210> SEQ ID NO 12
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 12

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Ala His Gly
            20                  25                  30

Pro Val Asn Trp Tyr Gln Gln Leu Pro Gly Thr Ala Pro Lys Leu Leu
        35                  40                  45

Ile Tyr Ala Thr Asn His Arg Pro Ser Gly Val Pro Asp Arg Phe Ser
    50                  55                  60

Gly Ser Lys Ser Gly Thr Thr Ala Ser Leu Thr Ile Ser Gly Leu Gln
65                  70                  75                  80

Ser Glu Asp Glu Ala Asp Tyr Tyr Cys Ala Ala Tyr Asp Leu Thr Gly
                85                  90                  95

Trp Phe Ala Tyr Ala Val Phe Gly Gly Thr Lys Leu Thr Val Leu
            100                 105                 110

<210> SEQ ID NO 13
<211> LENGTH: 675
<212> TYPE: DNA
<213> ORGANISM: Artificial Sequence
<220> FEATURE:
<223> OTHER INFORMATION: Synthetic Polynucleotide

<400> SEQUENCE: 13
cagcctgtgc tgactcagcc ggtttccctc tctgcatctc ctggagcatc agtcagtctc      60
acctgcacct tgcgcagtga catcagggtt agagattaca ggatattctg gtaccagcag     120
aagccaggga gtcctcccca gtatctcctg aggtacaaaa ccgactcaga taagcagcag     180
ggctctggag tccccagccg cttctctggg tccaaagatg cttcggccaa tgcagggatt     240
ttactcatct ctgggctcca gtctgaggat gaggctgact attactgtat gatttggcac     300
cgcaccacgg gcactagtct tgtgttcggc ggagggacca agctgaccgt cctaggtcag     360
cccaaggctg cccccctcgg tcactctgtt cccgccctcct ctgaggagct tcaagccaac     420
aaggccacac tggtgtgtct cataagtgac ttctacccgg gagccgtgac agtggcttgg     480
aaagcagata gcagccccgt caaggcggga gtggagacca ccacaccctc caaacaaagc     540
aacaacaagt acgcggccag cagctatctg agcctgacgc ctgagcagtg gaagtcccac     600
agaagctaca gctgccaggt cacgcatgaa gggagcaccg tggagaagac agtggcccct     660
acagaatgtt cataa                                                     675

<210> SEQ ID NO 14
<211> LENGTH: 224
<212> TYPE: PRT
<213> ORGANISM: Artificial Sequence
<220> FEATURE:
<223> OTHER INFORMATION: Synthetic Polypeptide

<400> SEQUENCE: 14

Gln Pro Val Leu Thr Gln Pro Val Ser Leu Ser Ala Ser Pro Gly Ala
1               5                   10                  15

```
Ser Val Ser Leu Thr Cys Thr Leu Arg Ser Asp Ile Arg Val Arg Asp
            20                  25                  30

Tyr Arg Ile Phe Trp Tyr Gln Gln Lys Pro Gly Ser Pro Pro Gln Tyr
        35                  40                  45

Leu Leu Arg Tyr Lys Thr Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Arg Thr Thr Gly Thr Ser Leu Val Phe Gly Gly Gly
            100                 105                 110

Thr Lys Leu Thr Val Leu Gly Gln Pro Lys Ala Ala Pro Ser Val Thr
        115                 120                 125

Leu Phe Pro Pro Ser Ser Glu Glu Leu Gln Ala Asn Lys Ala Thr Leu
    130                 135                 140

Val Cys Leu Ile Ser Asp Phe Tyr Pro Gly Ala Val Thr Val Ala Trp
145                 150                 155                 160

Lys Ala Asp Ser Ser Pro Val Lys Ala Gly Val Glu Thr Thr Thr Pro
                165                 170                 175

Ser Lys Gln Ser Asn Asn Lys Tyr Ala Ala Ser Ser Tyr Leu Ser Leu
            180                 185                 190

Thr Pro Glu Gln Trp Lys Ser His Arg Ser Tyr Ser Cys Gln Val Thr
        195                 200                 205

His Glu Gly Ser Thr Val Glu Lys Thr Val Ala Pro Thr Glu Cys Ser
    210                 215                 220

<210> SEQ ID NO 15
<211> LENGTH: 354
<212> TYPE: DNA
<213> ORGANISM: Artificial Sequence
<220> FEATURE:
<223> OTHER INFORMATION: Synthetic Polynucleotide

<400> SEQUENCE: 15
cagcctgtgc tgactcagcc ggtttccctc tctgcatctc ctggagcatc agtcagtctc      60
acctgcacct tgcgcagtga catcagggtt agagattaca ggatattctg gtaccagcag     120
aagccaggga gtcctcccca gtatctcctg aggtacaaaa ccgactcaga taagcagcag    180
ggctctggag tccccagccg cttctctggg tccaaagatg cttcggccaa tgcagggatt    240
ttactcatct ctgggctcca gtctgaggat gaggctgact attactgtat gatttggcac    300
cgcaccacgg gcactagtct tgtgttcggc ggagggacca agctgaccgt ccta          354

<210> SEQ ID NO 16
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 16

Gln Pro Val Leu Thr Gln Pro Ser Leu Ser Ala Ser Pro Gly Ala
1               5                   10                  15

Ser Val Ser Leu Thr Cys Thr Leu Arg Ser Asp Ile Arg Val Arg Asp
            20                  25                  30

Tyr Arg Ile Phe Trp Tyr Gln Gln Lys Pro Gly Ser Pro Pro Gln Tyr
        35                  40                  45
```

```
Leu Leu Arg Tyr Lys Thr Asp Ser Asp Lys Gln Gln Gly Ser Gly Val
        50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His Arg Thr Thr Gly Thr Ser Leu Val Phe Gly Gly Gly
            100                 105                 110

Thr Lys Leu Thr Val Leu
        115
```

<210> SEQ ID NO 17
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 17

```
tcctatgtgc tgactcagcc accctcagtg tcagtggccc caggaaagac ggccaggatt      60
acctgtgggg gaaacaaaat tggacaccgc gccgtgcact ggtaccagca gaagccaggc     120
caggcccctg tgctggtcat ctattatacc tatgagcggc cctcagggat tcctgagcga     180
ttctctggct ccaactctgg gaacacggcc accctgacca tcagcagggt cgaagccggg     240
gatgaggccg actattactg tcaggtgtgg gattggtaca gcgagggggg ggttgtgttc     300
ggcggaggga ccaagctgac cgtcctaggt cagcccaagg ctgccccctc ggtcactctg     360
ttcccgccct cctctgagga gcttcaagcc aacaaggcca cactggtgtg tctcataagt     420
gacttctacc cgggagccgt gacagtggct tggaaagcag atagcagccc cgtcaaggcg     480
ggagtggaga ccaccacacc ctccaaacaa agcaacaaca gtacgcggc cagcagctat     540
ctgagcctga cgcctgagca gtggaagtcc cacagaagct acagctgcca ggtcacgcat     600
gaagggagca ccgtggagaa gacagtggcc cctacagaat gttcataa              648
```

<210> SEQ ID NO 18
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 18

```
Ser Tyr Val Leu Thr Gln Pro Pro Ser Val Ser Val Ala Pro Gly Lys
 1               5                  10                  15

Thr Ala Arg Ile Thr Cys Gly Gly Asn Lys Ile Gly His Arg Ala Val
            20                  25                  30

His Trp Tyr Gln Gln Lys Pro Gly Gln Ala Pro Val Leu Val Ile Tyr
        35                  40                  45

Tyr Thr Tyr Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Trp Tyr Ser Glu Gly
                 85                  90                  95

Gly Val Val Phe Gly Gly Gly Thr Lys Leu Thr Val Leu Gly Gln Pro
            100                 105                 110
```

```
Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 19
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 19
tcctatgtgc tgactcagcc accctcagtg tcagtggccc caggaaagac ggccaggatt     60
acctgtgggg gaaacaaaat tggacaccgc gccgtgcact ggtaccagca gaagccaggc    120
caggcccctg tgctggtcat ctattatacc tatgagcggc cctcagggat cctgagcga    180 ttctctggct ccaactctgg gaacacggcc accctgacca tcagcagggt cgaagccggg    240
gatgaggccg actattactg tcaggtgtgg gattggtaca gcgagggggg ggttgtgttc    300
ggcggaggga ccaagctgac cgtccta                                         327

<210> SEQ ID NO 20
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 20

Ser Tyr Val Leu Thr Gln Pro Pro Ser Val Ser Val Ala Pro Gly Lys
1               5                   10                  15

Thr Ala Arg Ile Thr Cys Gly Gly Asn Lys Ile Gly His Arg Ala Val
            20                  25                  30

His Trp Tyr Gln Gln Lys Pro Gly Gln Ala Pro Val Leu Val Ile Tyr
        35                  40                  45

Tyr Thr Tyr Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Trp Tyr Ser Glu Gly
                85                  90                  95

Gly Val Val Phe Gly Gly Gly Thr Lys Leu Thr Val Leu
            100                 105

<210> SEQ ID NO 21
<211> LENGTH: 657
<212> TYPE: DNA
<213> ORGANISM: Artificial Sequence
```

```
<220> FEATURE:
<223> OTHER INFORMATION: Synthetic Polynucleotide

<400> SEQUENCE: 21
aattttatgc tgactcagcc ccactctgtg tcggagtctc cggggaagac ggtaaccatc      60
tcctgcaccc gcagcagtgg ctctatcgaa gataagtatg tgcagtggta ccagcagcgc     120
ccgggcagtt cccccaccat tgtgatctat tatgataacg aaagaccctc tggggtccct     180
gatcggttct ctggctccat cgacagctcc tccaactctg cctccctcac catctctgga     240
ctgaagactg aggacgaggc tgactactac tgtcagacct acgaccagag cctgtatggt     300
tgggtgttcg gcggagggac caagctgacc gtcctaggtc agcccaaggc tgccccctcg     360
gtcactctgt tcccgccctc ctctgaggag cttcaagcca acaaggccac actggtgtgt     420
ctcataagtg acttctaccc gggagccgtg acagtggctt ggaaagcaga tagcagcccc     480
gtcaaggcgg gagtggagac caccacaccc tccaaacaaa gcaacaacaa gtacgcggcc     540
agcagctatc tgagcctgac gcctgagcag tggaagtccc acagaagcta cagctgccag     600
gtcacgcatg aagggagcac cgtggagaag acagtggccc ctacagaatg ttcataa       657

<210> SEQ ID NO 22
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 22

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Glu Asp Lys
            20                  25                  30

Tyr Val Gln Trp Tyr Gln Gln Arg Pro Gly Ser Ser Pro Thr Ile Val
        35                  40                  45

Ile Tyr Tyr Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Gln
                85                  90                  95

Ser Leu Tyr Gly Trp Val Phe Gly Gly Gly Thr Lys Leu Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215
```

<210> SEQ ID NO 23
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 23

```
aattttatgc tgactcagcc ccactctgtg tcggagtctc cggggaagac ggtaaccatc    60
tcctgcaccc gcagcagtgg ctctatcgaa gataagtatg tgcagtggta ccagcagcgc   120
ccgggcagtt cccccaccat tgtgatctat tatgataacg aaagaccctc tggggtccct   180
gatcggttct ctggctccat cgacagctcc tccaactctg cctccctcac catctctgga   240
ctgaagactg aggacgaggc tgactactac tgtcagacct acgaccagag cctgtatggt   300
tgggtgttcg gcggagggac caagctgacc gtccta                             336
```

<210> SEQ ID NO 24
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 24

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Glu Asp Lys
            20                  25                  30

Tyr Val Gln Trp Tyr Gln Gln Arg Pro Gly Ser Ser Pro Thr Ile Val
        35                  40                  45

Ile Tyr Tyr Asp Asn Glu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Thr Tyr Asp Gln
                85                  90                  95

Ser Leu Tyr Gly Trp Val Phe Gly Gly Gly Thr Lys Leu Thr Val Leu
            100                 105                 110
```

<210> SEQ ID NO 25
<211> LENGTH: 648
<212> TYPE: DNA
<213> ORGANISM: Artificial Sequence
<220> FEATURE:
<223> OTHER INFORMATION: Synthetic Polynucleotide

<400> SEQUENCE: 25

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag atgcaccecgc gcgccccgaa gaccttcggc   300
caagggacca aggtggaaat caaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
```
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacagggag agtgttaa                 648

<210> SEQ ID NO 26
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 26

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met His Pro Arg Ala Pro
                 85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 27
<211> LENGTH: 324
<212> TYPE: DNA
<213> ORGANISM: Artificial Sequence
<220> FEATURE:
<223> OTHER INFORMATION: Synthetic Polynucleotide

<400> SEQUENCE: 27
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcagcag atgcaccgc gcgcccccgaa gaccttcggc    300 caagggacca aggtggaaat caaa                                          324

<210> SEQ ID NO 28
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met His Pro Arg Ala Pro
                85                  90                  95

Lys Thr Phe Gly Gln Gly Thr Lys Val Glu Ile Lys
            100                 105

<210> SEQ ID NO 29
<211> LENGTH: 678
<212> TYPE: DNA
<213> ORGANISM: Artificial Sequence
<220> FEATURE:
<223> OTHER INFORMATION: Synthetic Polynucleotide

<400> SEQUENCE: 29
cagcctgtgc tgactcagcc ggcttccctc tctgcatctc ctggggcatc agccagtctc      60
acctgcacct tgcgcagtgg catcaacgtt agagattaca ggatattctg gtaccagcag     120
aagccaggga gtcctcccca gtatctcctg aggtacaaaa gcgcatcaga taagcagcag    180
ggctctggag tccccagccg cttctctggg tccaaagatg cttcggccaa tgcagggatt     240
ttactcatct ctgggctcca gtctgaggat gaggctgact attactgtat gatttggcac     300
cacgattcgg aggggcatgc ttttgtgttc ggcggaggga ccaagctgac cgtcctaggt    360
cagcccaagg ctgccccctc ggtcactctg ttcccgccct cctctgagga gcttcaagcc    420
aacaaggcca cactggtgtg tctcataagt gacttctacc cgggagccgt gacagtggct    480
tggaaagcag atagcagccc cgtcaaggcg ggagtggaga ccaccacacc ctccaaacaa    540
agcaacaaca gtacgcggc cagcagctat ctgagcctga cgcctgagca gtggaagtcc     600
cacagaagct acagctgcca ggtcacgcat gaagggagca ccgtggagaa gacagtggcc    660
cctacagaat gttcataa                                                   678

<210> SEQ ID NO 30
<211> LENGTH: 225
<212> TYPE: PRT
<213> ORGANISM: Artificial Sequence
<220> FEATURE:
<223> OTHER INFORMATION: Synthetic Polypeptide

<400> SEQUENCE: 30

Gln Pro Val Leu Thr Gln Pro Ala Ser Leu Ser Ala Ser Pro Gly Ala
1               5                   10                  15

```
Ser Ala Ser Leu Thr Cys Thr Leu Arg Ser Gly Ile Asn Val Arg Asp
             20                  25                  30

Tyr Arg Ile Phe Trp Tyr Gln Gln Lys Pro Gly Ser Pro Pro Gln Tyr
         35                  40                  45

Leu Leu Arg Tyr Lys Ser Ala Ser Asp Lys Gln Gln Gly Ser Gly Val
     50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His His Asp Ser Glu Gly His Ala Phe Val Phe Gly Gly
            100                 105                 110

Gly Thr Lys Leu Thr Val Leu Gly Gln Pro Lys Ala Ala Pro Ser Val
        115                 120                 125

Thr Leu Phe Pro Pro Ser Ser Glu Glu Leu Gln Ala Asn Lys Ala Thr
    130                 135                 140

Leu Val Cys Leu Ile Ser Asp Phe Tyr Pro Gly Ala Val Thr Val Ala
145                 150                 155                 160

Trp Lys Ala Asp Ser Ser Pro Val Lys Ala Gly Val Glu Thr Thr Thr
                165                 170                 175

Pro Ser Lys Gln Ser Asn Asn Lys Tyr Ala Ala Ser Ser Tyr Leu Ser
            180                 185                 190

Leu Thr Pro Glu Gln Trp Lys Ser His Arg Ser Tyr Ser Cys Gln Val
        195                 200                 205

Thr His Glu Gly Ser Thr Val Glu Lys Thr Val Ala Pro Thr Glu Cys
    210                 215                 220

Ser
225

<210> SEQ ID NO 31
<211> LENGTH: 357
<212> TYPE: DNA
<213> ORGANISM: Artificial Sequence
<220> FEATURE:
<223> OTHER INFORMATION: Synthetic Polynucleotide

<400> SEQUENCE: 31
cagcctgtgc tgactcagcc ggcttccctc tctgcatctc ctggggcatc agccagtctc      60
acctgcacct tgcgcagtgg catcaacgtt agagattaca ggatattctg gtaccagcag     120
aagccaggga gtcctcccca gtatctcctg aggtacaaaa gcgcatcaga taagcagcag    180
ggctctggag tccccagccg cttctctggg tccaaagatg cttcggccaa tgcagggatt     240
ttactcatct ctgggctcca gtctgaggat gaggctgact attactgtat gatttggcac    300
cacgattcgg agggggcatgc ttttgtgttc ggcggaggga ccaagctgac cgtccta      357

<210> SEQ ID NO 32
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 32

Gln Pro Val Leu Thr Gln Pro Ala Ser Leu Ser Ala Ser Pro Gly Ala
 1               5                  10                  15

Ser Ala Ser Leu Thr Cys Thr Leu Arg Ser Gly Ile Asn Val Arg Asp
             20                  25                  30
```

```
Tyr Arg Ile Phe Trp Tyr Gln Gln Lys Pro Gly Ser Pro Pro Gln Tyr
        35                  40                  45

Leu Leu Arg Tyr Lys Ser Ala Ser Asp Lys Gln Gln Gly Ser Gly Val
    50              55                  60

Pro Ser Arg Phe Ser Gly Ser Lys Asp Ala Ser Ala Asn Ala Gly Ile
65              70                  75                      80

Leu Leu Ile Ser Gly Leu Gln Ser Glu Asp Glu Ala Asp Tyr Tyr Cys
                85                  90                  95

Met Ile Trp His His Asp Ser Glu Gly His Ala Phe Val Phe Gly Gly
            100                 105                 110

Gly Thr Lys Leu Thr Val Leu
        115
```

GENERATING MULTISPECIFIC ANTIBODY MIXTURES AND METHODS OF USES THEREOF

RELATED APPLICATIONS

This application claims the benefit of U.S. Provisional Application No. 62/535,354, filed Jul. 21, 2017, the contents of which are incorporated herein by reference in its entirety.

INCORPORATION-BY-REFERENCE OF SEQUENCE LISTING

The contents of the file named NOVI-045_001US_322145-2715_SequenceListing_ST25.txt", which was created on Aug. 30, 2018, and is 40 KB in size are hereby incorporated by reference in their entirety.

FIELD OF THE INVENTION

The invention relates to the generation of multispecific antibody mixtures include a subset of antibodies isolated from a mixture of two or more monospecific antibodies and one or more bispecific antibodies, wherein all antibodies in the subset have the same common heavy chain. The invention also relates to methods of isolating, purifying, or otherwise producing such a subset of antibodies by using at least one affinity chromatography step. The invention also relates to methods of using such a subset of antibodies in a variety of therapeutic indications.

BACKGROUND OF THE INVENTION

During the last two decades, monoclonal antibodies (mAbs) have become an important therapeutic modality, bringing significant benefits for patients in various indications. The success of mAbs is in part due to their high specificity for their target antigen and low intrinsic toxicity. These properties greatly limit off-target side effects when compared to other classes of drugs. The vast majority of approved therapeutic mAbs are unmodified antibodies of the IgG isotype.

However, the targeting of a single protein that is enabled by standard mAbs might not always be sufficient to achieve significant therapeutic effect (Fischer Expert Opin. Drug Discov. 2008 3(8):833-839).

An obvious option to increase efficacy, is to use two mAbs in combination. This strategy is clinically pursued, for instance, for antibodies targeting immune checkpoint molecules such as anti-CTLA4 and anti-PD-1 antibodies (Larkin et al., N Engl J Med 2015; 373:23-34; Harris et al., Cancer Biol Med. 2016 13(2):171-93). However, significant cost and development hurdles are associated with the development of mAbs combinations. In particular, two separate manufacturing processes have to be put in place, leading to significant increase in costs (Rasmussen et al., Archives of Biochemistry and Biophysics 2012 526:39-145). These issues become even more important if targeting three or more proteins or antigens is considered.

Several approaches for targeting multiple proteins or antigens have been used to date. The use of two mAbs in combination has been pursued, but is often hindered by significant cost and development hurdles. Bispecific antibodies (BiAbs) represent a rapidly developing alternative to achieve multispecific targeting and over 60 formats have been described to date (Spiess et al., Mol Immunol. 2015 67:95-106; Brinkmann and Kontermann mAbs 2017 9:182-212), and another approach to achieve targeting of two or even more proteins is the generation of antibody mixtures or recombinant polyclonal mixtures. However, only a few of these multispecific formats have been approved for therapeutic use.

Accordingly, there exists a need for generating multispecific antibody mixtures that are able to target multiple proteins, epitopes, and/or antigens.

SUMMARY OF THE INVENTION

The disclosure provides antibody mixtures that include a subset of antibodies isolated from a mixture of two or more monospecific antibodies and one or more bispecific antibodies, wherein all antibodies in the subset have the same common heavy chain. These mixtures are produced when multiple light chains are co-expressed with a common heavy chain in a single cell. In some embodiments, the purified subsets include only antibodies that contain at least a kappa light chain. In some embodiments, the purified subsets include only antibodies that contain at least a lambda light chain. In some embodiments, the purified subsets include only antibodies that contain a kappa light chain and a lambda light chain.

The disclosure also provides methods of isolating, purifying, or otherwise producing a subset of antibodies isolated from a mixture of two or more monospecific antibodies and one or more bispecific antibodies, wherein all antibodies in the subset have the same common heavy chain, by using at least one affinity chromatography step. In some embodiments, the purification step is performed using kappa constant or variable domain specific affinity chromatography media. In some embodiments, the purification step is performed using lambda constant or variable domain specific affinity chromatography media. In some embodiments, the purification step is performed using a two-step affinity chromatography process. In some embodiments, the first purification step is performed using kappa constant or variable domain specific affinity chromatography media and the second purification step using lambda constant specific affinity chromatography media. In some embodiments, the first purification step is performed using Lambda constant specific affinity chromatography media and the second purification step using Kappa constant or variable domain specific affinity chromatography media.

The multispecific antibody mixtures and methods provided herein are useful in any of a variety of therapeutic, diagnostic, and/or prophylactic indications. For example, the multispecific antibody mixtures are useful in treating, preventing and/or delaying the progression of, or alleviating a symptom of cancer or other neoplastic condition by administering an antibody mixture to a subject in which such treatment or prevention is desired. In some embodiments, the multispecific antibody mixtures described herein are useful in treating hematological malignancies and/or solid tumors. For example, the multispecific antibody mixtures described herein are useful in treating CD47$^+$ tumors, mesothelin$^+$ tumors, and combinations thereof. By way of non-limiting example, the multispecific antibody mixtures described herein are useful in treating non-Hodgkin's lymphoma (NHL), acute lymphocytic leukemia (ALL), acute myeloid leukemia (AML), chronic lymphocytic leukemia (CLL), chronic myelogenous leukemia (CIVIL), multiple myeloma (MM), breast cancer, ovarian cancer, head and neck cancer, bladder cancer, melanoma, mesothelioma, colorectal cancer, cholangiocarcinoma, pancreatic cancer, including pancreatic adenocarcinoma, lung cancer, including lung adenocarcinoma, leiomyoma, leiomyosarcoma, kidney cancer, glioma, glioblastoma, endometrial cancer, esophageal cancer, biliary gastric cancer, and prostate cancer. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

In some embodiments, the multispecific antibody mixtures are useful in treating, preventing and/or delaying the progression of, or alleviating a symptom of an autoimmune disease and/or inflammatory disorder by administering an antibody mixture to a subject in which such treatment or prevention is desired. Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis juvenile, discoid lupus, essential mixed cryoglobulinemia, fibromyalgia-fibromyositis, Graves' disease, Guillain-Barr-syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, chronic obstructive pulmonary disease, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In some embodiments, the multispecific antibody mixtures are useful in retargeting T cells.

Pharmaceutical compositions according to the invention can include a multispecific antibody mixture of the invention and a carrier. These pharmaceutical compositions can be included in kits, such as, for example, therapeutic kits and/or diagnostic kits.

BRIEF DESCRIPTION OF THE DRAWINGS

FIG. 1A depicts methods of mixing monoclonal antibodies (mAbs) that were expressed and purified independently to produce a mixture of mAbs. FIG. 1B depicts methods of mixing cell lines, also referred to as a polyclonal cell bank, to produce a mixture of only mAbs in a single fermentation reactor. FIG. 1C depicts methods of co-expressing multiple antibody chains in a single cell line to produce a mixture of mAbs and bispecific antibodies (BiAbs).

FIG. 2A depicts how the co-expression of two antibody light chains with a single heavy chain results in secretion of three different antibodies: two mAbs each incorporating the same light chain in each Fab and a single BiAb incorporating a different light chain in each Fab. FIG. 2B depicts how the co-expression of three antibody light chains with a single heavy chain results in secretion of six different antibodies: three mAbs each incorporating the same light chain in each Fab and three BiAb incorporating a different light chain in each Fab. FIG. 2C depicts how the co-expression of four antibody light chains with a single heavy chain results in secretion of ten different antibodies: four mAbs each incorporating the same light chain in each Fab and six BiAb incorporating a different light chain in each Fab.

FIG. 3 is a schematic representation of methods of co-expressing two lambda light chains, one kappa light chain, and a single common heavy chain in a single cell, which results in the secretion of a mixture of two IgGλλ mAbs, one IgGκκ mAb, two IgGκλ BiAbs, and one IgGλλ BiAb (Mixture 1). From Mixture 1, different submixtures can be isolated using different affinity chromatography steps as indicated.

DETAILED DESCRIPTION

Figure 1A:
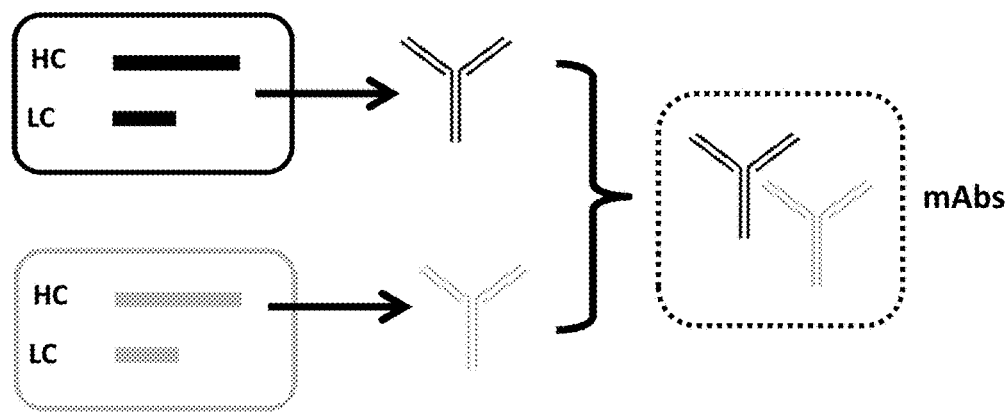
FIGS. 1A, 1B, and 1C are a series of schematic representations of various approaches to generate recombinant antibody mixtures.

The multispecific antibody mixtures and methods provided herein overcome limitations seen with other antibody formats and/or antibody mixtures. Currently, most of the approved monoclonal antibody formats are unmodified antibodies of the IgG1 isotype. However, targeting a single antigen is not always sufficient to achieve the desired therapeutic effects (Fischer Expert Opin. Drug Discov. 2008 3(8):833-839). Two mAbs in combination have been used to increase efficiency. This strategy is clinically pursued, for instance, for antibodies targeting immune checkpoint molecules such as anti-CTLA4 and anti-PD-1 antibodies (Larkin et al., N Engl J Med 2015; 373:23-34; Harris et al., Cancer Biol Med. 2016 13(2):171-93). However, significant cost and development hurdles are associated with the development of mAbs combinations. In particular, two separate manufacturing processes have to be put in place, leading to significant increase in costs (Rasmussen et al., Archives of Biochemistry and Biophysics 2012 526:39-145). These issues become even more important if targeting three or more proteins or antigens is considered.

Bispecific antibodies (BiAbs) have been developed as an alternative means to achieve multispecific targeting, and over 60 formats have been described to date (Spiess et al., Mol Immunol. 2015 67:95-106; Brinkmann and Kontermann mAbs 2017 9:182-212). As two binding sites are incorporated into the same molecule, unique modes of actions that are not supported by mAbs or mAb combinations, are enabled by BiAbs (Fischer and Leger Pathobiology. 2007 74(1):3-14). Examples of such unique modes of action are retargeting of T-cell or NK cells to tumors cells, BiAb delivery to the central nervous system via increased transportation across the blood brain barrier, coagulation Factor VIII mimetic activity, selective targeting of receptors expressed on multiple cell types.

Yet another approach to achieve targeting of two or even more proteins is the generation of antibody mixtures or recombinant polyclonal mixtures. In contrast to a combination of two mAbs described above, in which each mAb is produced separately, the antibodies in the mixture are produced together as a mixture. Various approaches to generate mixtures have been described (see e.g., Raju and Strohl Expert Opin. Biol. Ther. 2013 13(10):1347-1352; Wang et al., 2013 Current Opinion in Chemical Engineering 2013 2:1-11). A general challenge for the production of a recombinant polyclonal mixture, is to achieve consistency between batches so that each component of the mixtures remains constant and thus the overall composition and biological activity of the mixture is consistent.

In one approach, different stable cell lines, each expressing a single monoclonal antibody, are mixed top produce a polyclonal cell bank that is used in a single bioreactor for production. In this case, the different antibodies are secreted by different cell lines into the medium and all antibodies are purified together to obtain the final recombinant antibody mixture (Rasmussen et al., Archives of Biochemistry and Biophysics 2012 526:39-145). In this case, the reproducible growth and productivity characteristics of the individual cell lines during fermentation must be extremely well controlled to ensure consistency between batches of the recombinant polyclonal mixture. Faster growth or increased productivity of one cell line has a direct impact on the mixture composition. Achieving such a level of control is not straightforward and represents significant hurdle of this approach. Nevertheless, very complex mixtures of up to 25 independent antibodies have been developed using polyclonal cells lines and evaluated in clinical trials (Hjelmstrom et al., Blood 2008 112:1987).

Another strategy is to co-express multiple antibody heavy and/or light chains within a single cell. In this case, different heavy and light chains can pair and, thus, a mixture can be generated. The complexity of the resulting mixture depends on the number of different chain that are co-expressed. In this approach, ensuring that the different possible pairings reconstitute a functional antigen binding site is critical to avoid production of non-functional molecules. This pairing issue can be solved by the use of a common heavy or common light chain or by engineering of protein interfaces to preferentially form the desired pairing (See e.g., Fischer et al., Nat. Comms 20156:6113 doi: 10.1038/ncomms7113). In contrast to the previous approach relying on mixing of independent cell lines, this approach leads to the generation of both mAbs and BiAbs. A significant advantage is that, once a cell line expressing the different antibody chains in a stable manner is identified, the fermentation and production is simplified as it is similar to a standard mAb process. However, if all pairing are allowed, the complexity of the mixture components (mAbs and BiAbs) can be quite significant and thus antibodies relying on a common heavy or light chain are preferred.

Figure 1B:
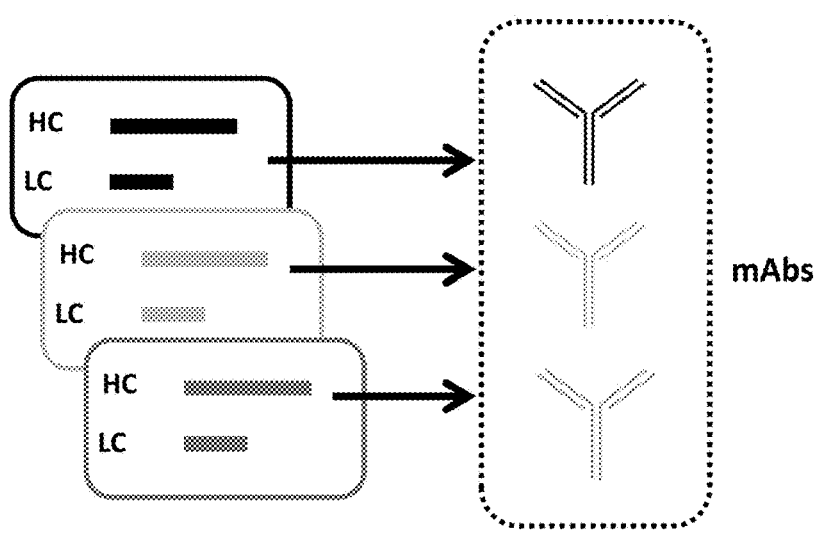
Figure 1C:
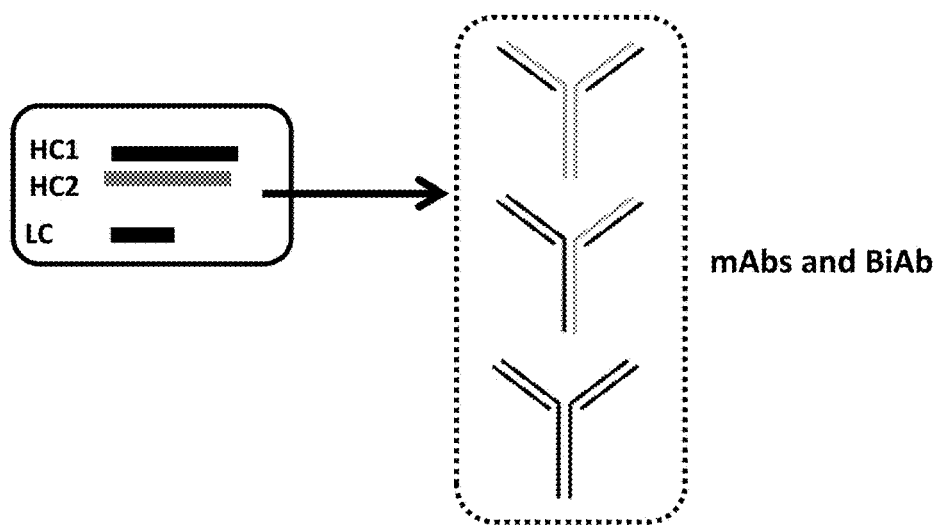

Different approaches to generate recombinant antibody mixtures, their benefits and limitations are listed in Table 1 and illustrated in FIGS. 1A-1C.

Mixtures enable unique modes of actions that cannot be achieved with a single antibody.

For instance, targeting the receptors of the HER/ErbB family has been actively explored with antibody mixtures. This family of receptor tyrosine kinases includes growth factor receptor EGFR/ErbB 1, HER-2/ErbB2, HER-3/ErbB3 and HER-4/ErbB4. Several monoclonal antibodies targeting EGFR and HER2 are approved for clinical use. Studies have reported that mixtures of antibodies targeting multiple epitopes and thus able to simultaneously engage these targets lead to increased inhibition of cancer cell growth in in vitro and in vivo experiments. This has led to the development of several antibody mixtures directed against members of the HER/ErbB family. One example is Sym004, a mixture of two anti EGFR mAbs that showed significantly superior activity in preclinical models compared to the approved anti-EGFR mAb Cetuximab (Koefoed et al., mAbs 2011 3:6, 584-595). MM-151 is another mixture that is composed of three human mAbs targeting distinct, non-overlapping epitopes on EGFR (Arena et al., Science Translational Medicine 2016 8(324), 324ra14). This mixture provides more effective blockade of the receptor and limits the emergence of resistance when compared to single mAb therapy. A more complex mixture, Sym013, composed of 6 mAbs targeting EGFR, HER2 and HER3 (two mAbs directed against non-overlapping epitope on each target), has also reached clinical development stage. The overall superior activity observed with mixtures against this receptor family can be explained by several factors such as a more complete shutdown of this partially redundant signaling pathways, increased internalization and degradation via antibody mediated receptor cross-linking, increase Fc-mediated cell killing.

Another therapeutic area in which antibody mixtures have demonstrated striking superiority is the treatment of infectious diseases (Oleksiewicz et al., Archives of Biochemistry and Biophysics 2012 526:124-131; Pohl et al., Infection and Immunity 2013 81(6):1880-1888). For instance, multi-

TABLE 1

Recombinant Antibody Mixtures

| Approach | Antibody forms present in the mixture | Benefits | Limitations and challenges |
| --- | --- | --- | --- |
| Mixing of purified monoclonal antibodies | mAbs | Composition can be precisely controlled by mixing purified mAbs | High cost of goods (COGs) due to independent manufacturing of each component before mixing This issue increases with each additional antibody composing in the mixture |
| Mix of cells lines (polyclonal cell bank) | mAbs | Complex mixtures can be achieved Reduced COGs | Control of fermentation reaction and polyclonal cell line stability are critical to ensure batch consistency |
| Co-expression of multiple antibody chains in a single cell line | mAbs and BiAbs | Single cell line is used as in standard mAb process Presence of BiAb that enable novel modes of action Reduced COGs | Use of common chain to ensure productive pairings |

Several mixtures have been developed using some of the approaches described above and have reached clinical stage indicating that this therapeutic modality is viable of interest.

epitope targeting of soluble toxins such as Botulinum toxin A increases not only neutralization of the toxin but also its clearance from circulation. Overall, mAb not proven very effective for the treatment of infections in contrast to other therapeutic areas. This might reflect that a polyclonal antibody response similar to that of the natural immune system is required for effective protection against complex organisms such as pathogens.

Rozrolimupab is a striking example of how complex antibody mixtures can. This mixture of 25 mAbs against the Rhesus D antigen is produced using the polyclonal cell bank approach, which is exemplified in FIG. 1B, and has been developed for the treatment of Immune thrombocytopenic purpura (ITP). A benefit of this complex mixture is that it provides effective coverage of the numerous Rhesus D variants present in the population (Robak et al., Blood. 2012 120(18): 3670-76).

These examples highlight the mechanistic advantages that mixtures can provide in comparison to single mAb therapy. These mechanisms include but are not limited to: increased internalization and degradation of receptors, fast and superior clearance of soluble targets, increased Fc-dependent effector functions, synergistic effect of targeting multiple epitopes on a single target or multiple targets and pathways, better coverage of target variants and prevention of escape mutations.

The present invention provides the mean of generating defined antibody mixture of either i) bispecific antibodies (BiAbs) only or ii) monoclonal antibodies (mAbs) and BiAbs. The method relies on co-expression of a single antibody heavy chain that is common to all Fv regions of the antibodies in the mixture and several light chains of either kappa or lambda families. This co-expression and random incorporation into IgG molecules leads to the secretion from a single cell of a mixture of monospecific mAbs or BiAb that all contain the same heavy chain. The complete mixture can then be purified using for instance an affinity reagent binding the Fc region of an IgG such Protein A, as previously described in US20140179547. The invention improves over previous methods as it allows to selectively purify different subsets of the secreted mixture. In particular, it allows for the simple and cost effective generation of mixtures of BiAbs. This opens the possibility of using mixtures of BiAbs for modes of action that are not enabled by a single mAb or mAb mixtures. The present invention combines the benefit of using a single production cell line and the possibility to control the composition of the final purified mixtures to maximize the desired biological activity.

Figure 2A:
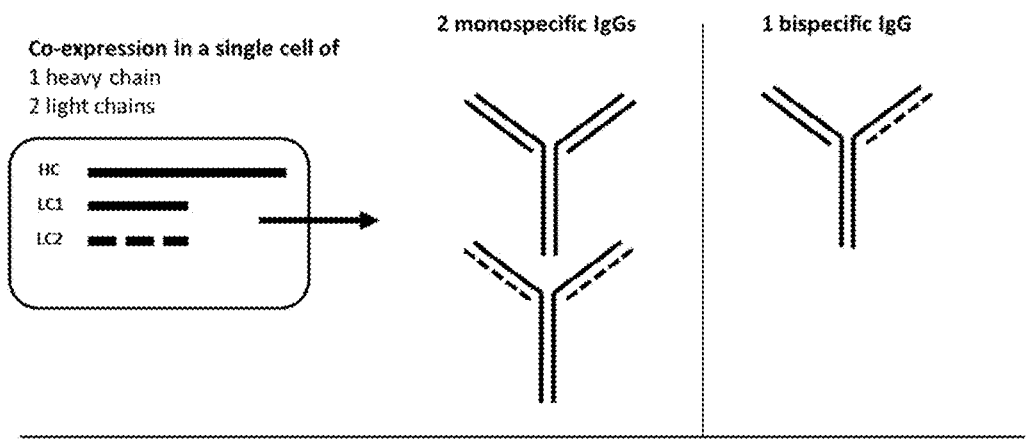
FIGS. 2A, 2B, and 2C are a series of schematic representations of methods of co-expressing multiple light chains with a single, common heavy chain and the resultant antibody mixtures produced.

Depending on the number of light chains that are co-expressed with a common heavy chain, different types of antibody mixtures can be generated. This process can be generalized as follows:

For
n=the number of different light chains expressed with a common heavy chain
Then
The number of different mAbs=n
The number of different BiAbs=$(n^2-n)/2$
The total number of different antibodies=$n+(n^2-n)/2$ Table 2 lists these numbers for the co-expression of 2 to 10 different light chains and 3 examples are further detailed below:

1—If two antibody light chains are co-expressed with a single heavy chain three different antibodies are secreted: two mAbs each incorporating the same light chain in each Fab and a single BiAb incorporating a different light chain in each Fab (see FIG. 2A). However, the abundance of the three forms depends on the relative expression and assembly of the two light chains. Provided expression and assembly are equivalent the theoretical distribution is 25% of each mAb and 50% of the BiAb.

Figure 2B:
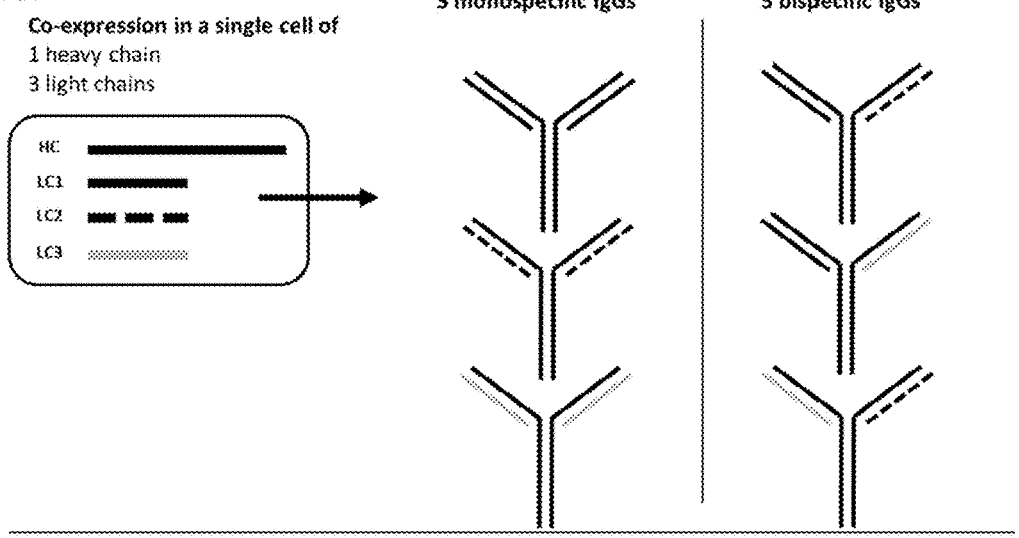

2—If three antibody light chains are co-expressed with a single heavy chain, 6 different antibodies are secreted: three mAbs each incorporating the same light chain in each Fab and three BiAb incorporating a different light chain in each Fab (see FIG. 2B). Provided expression and assembly are equivalent the theoretical distribution is 11.1% for each mAb and 22.2% for each of the BiAbs.

Figure 2C:
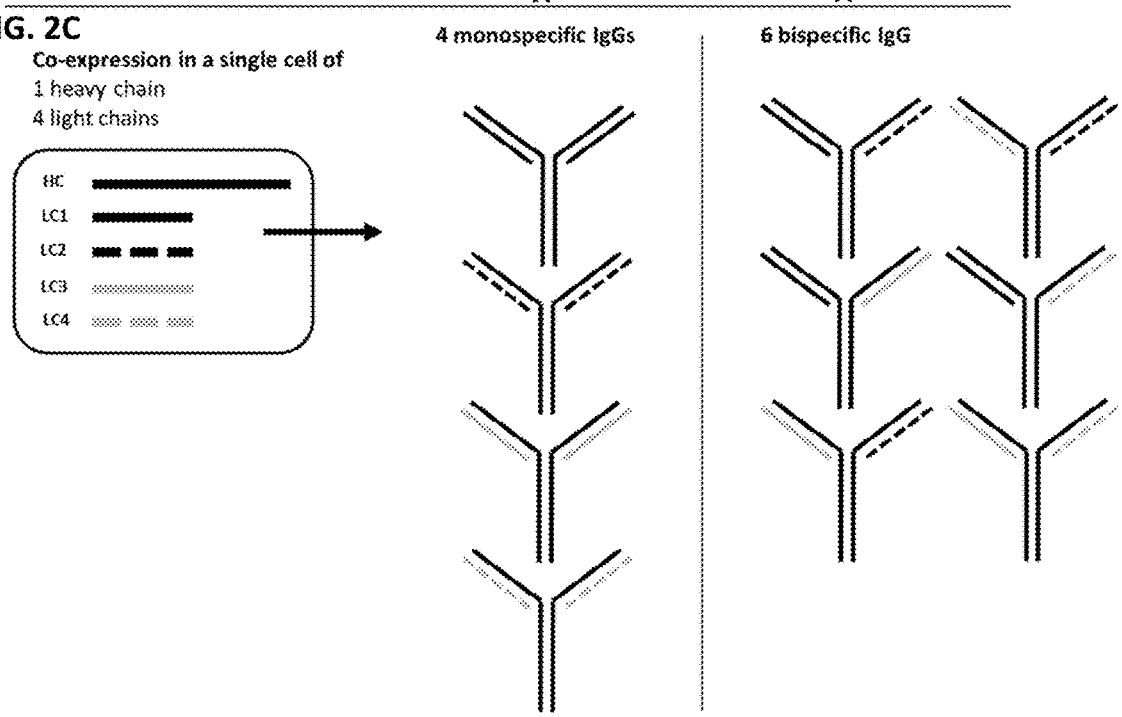

3—If four antibody light chains are co-expressed with a single heavy chain, 10 different antibodies are secreted: four mAbs each incorporating the same light chain in each Fab and six BiAb incorporating a different light chain in each Fab (see FIG. 2C). Provided expression and assembly are equivalent the theoretical distribution is 6.25% for each mAb and 12.5% for each of the BiAbs.

TABLE 2

Summary of Antibody Mixtures

| Number of light chains co-expressed (n) | Number of mAbs generated (n) | Number of BiAbs generated $(n^2 - n)/2$ | Total number of molecules generated $(n + (n^2 - n)/2)$ |
|---|---|---|---|
| 2 | 2 | 1 | 3 |
| 3 | 3 | 3 | 6 |
| 4 | 4 | 6 | 10 |
| 5 | 5 | 10 | 15 |
| 6 | 6 | 15 | 21 |
| 7 | 7 | 21 | 28 |
| 8 | 8 | 28 | 36 |
| 9 | 9 | 36 | 45 |
| 10 | 10 | 45 | 55 |

Figure 4:
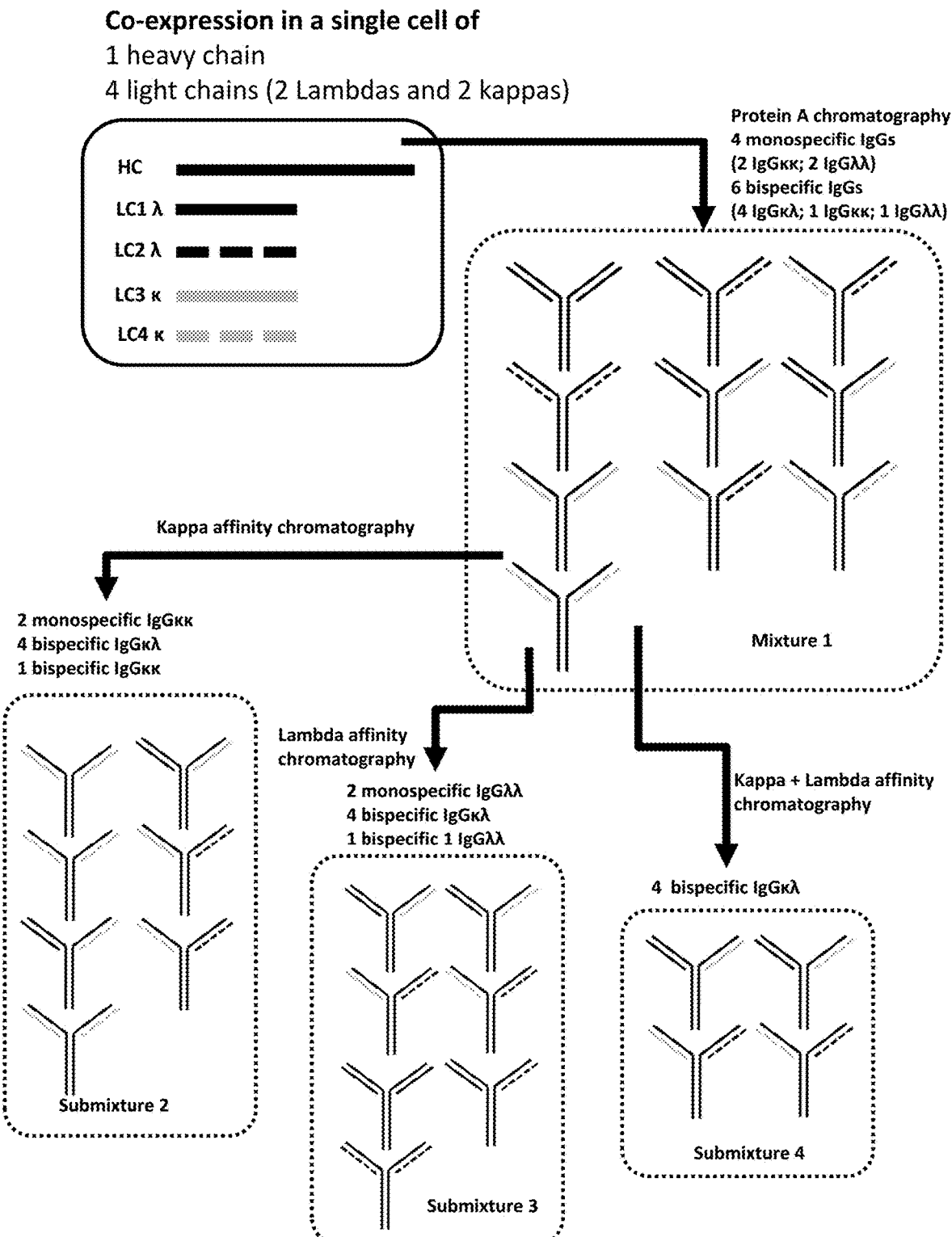
FIG. 4 is a schematic representation of methods of co-expressing two lambda light chains, two kappa light chains, and a single common heavy chain in a single cell, which results in the secretion of two IgGλλ mAbs, two IgGκκ mAbs, four IgGκλ BiAbs, one IgGλλ BiAb and one IgGκκ BiAb (Mixture 1). From Mixture 1, different submixtures can be isolated using different affinity chromatography steps as indicated.
Figure 5:
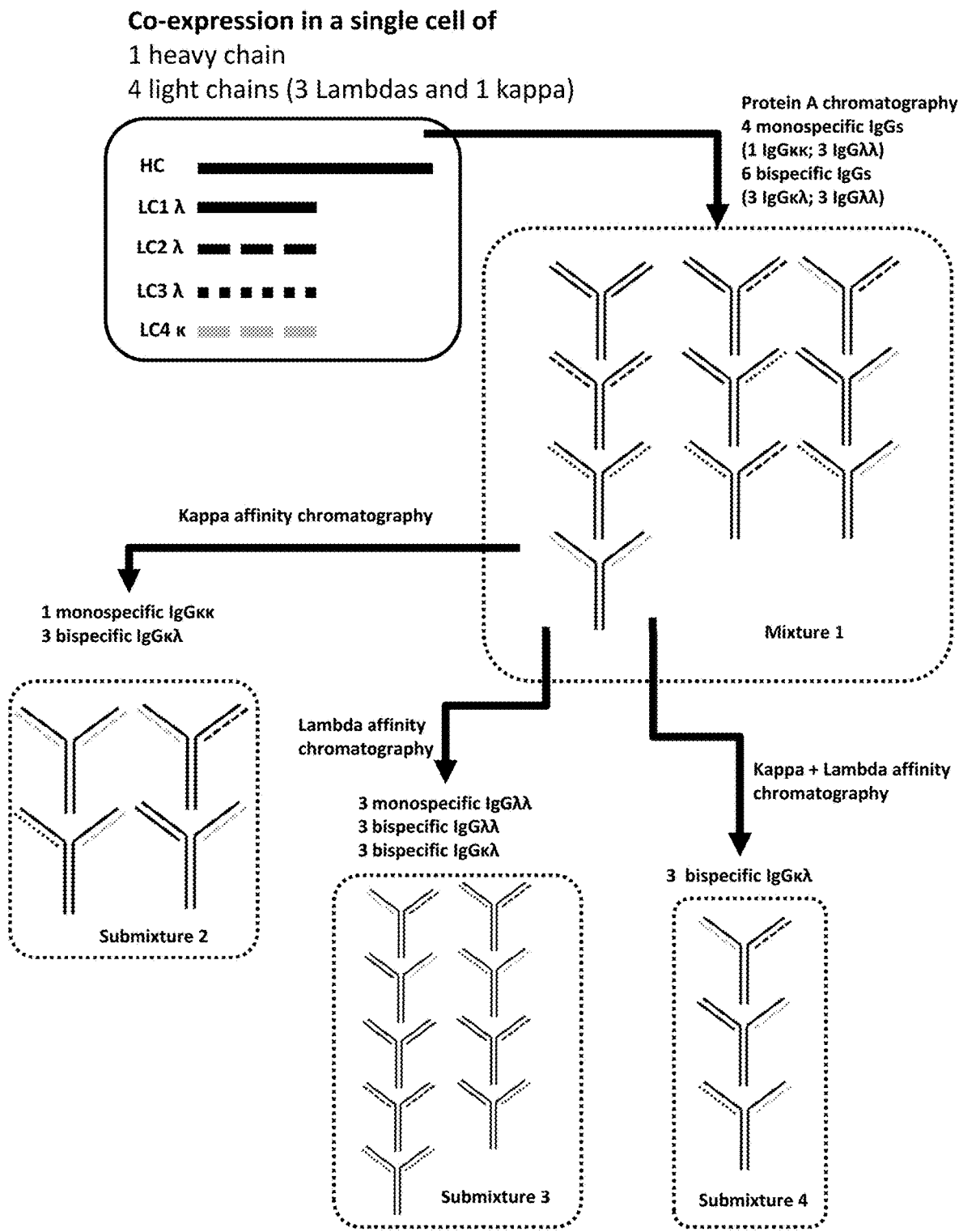
FIG. 5 is a schematic representation of methods of co-expressing three lambda light chains, one kappa light chain, and a single common heavy chain in a single cell, which results in the secretion of a mixture of three IgGλλ mAbs, one IgGκκ mAb, three IgGκλ BiAbs, three IgGλλ BiAb and one IgGκκ BiAb (Mixture 1). From Mixture 1, different submixtures can be isolated using different affinity chromatography steps as indicated.

Depending on whether the different light chains that are co-expressed are of the kappa type or of the lambda type, the distribution of mAbs and BiAbs containing kappa or lambda light chains will vary, thus further diversifying the types of mixtures that can be generated by this approach. For instance, if two lambda light chains and one kappa light chain are co-expressed with a common heavy chain, two IgGλλ mAbs, one IgGκκ mAb, two IgGκλ BiAbs, and one IgGλλ BiAb will be produced as shown in FIG. 3. If four light chain are co-expressed, the molecule distribution will vary if two kappa and two lambda light chains are used (FIG. 4) or if three lambdas and one kappa light chains are used (FIG. 5).

The resulting number of antibody forms generated in a given multispecific mixture can be generalized as follows:
For
n=number of kappa light chains
m=number of lambda light chains
Then
The number of IgGκκ mAbs=n
The number of IgGλλ mAbs=m
The number of IgGκλ BiAbs=n×m
The number of IgGκκ BiAbs=$(n^2-n)/2$
The number of IgGλλ BiAbs=$(m^2-m)/2$ Provided expression and assembly of the different light chains is identical, the resulting theoretical distribution of each form can be generalized as follows:
For
n=number of kappa light chains
m=number of lambda light chains Then
  The proportion of IgGκκ mAbs=n/(n×m)
  The proportion of IgGλλ mAbs=m/(n×m)
  The proportion of IgGκλ BiAbs=(n×m)×2/(n×m)
  The proportion of IgGκκ BiAbs=$(n^2-n)$/(n×m)
  The proportion of IgG) BiAbs=$(m^2-m)$/(n×m)

The present invention provides the mean of purifying a well-defined subset of either i) BiAbs only or ii) mAbs and BiAb from a wide variety of different mixtures that can be generated by the co-expression of varying numbers of kappa and or lambda light chains, as described above. The invention relies on multistep affinity chromatography using resins that bind specifically to the Fc portion and resins that bind specifically to the kappa constant region or lambda constant region. In this way, subsets of antibody forms composing these complex mixtures can be readily isolated and their composition tailored depending on which type of resins are used and the desired mode of action.

For instance, the co-expression of two lambda light chains and one kappa light chain with a common heavy chain generates a mixture that is composed of two IgGλλ mAbs, one IgGκκ mAb, two IgGκλ BiAbs, and one IgGλλ BiAb (FIG. 3). All these antibody forms contain an Fc portion and can be easily and effectively purified using, for instance, Protein A chromatography. From this mixture (Mixture 1, indicated in FIG. 3), different defined subsets of antibodies can be readily isolated using affinity chromatography media binding specifically either to the kappa or lambda chain, thereby allowing for capture of all antibody forms containing at least one kappa or lambda chain, respectively (see FIG. 3, submixtures 2 and 3, respectively). Submixture 2 will contain one IgGκκ mAb and two IgGκλ BiAbs. Submixture 3 will contain two IgGλλ mAbs, two IgGκλ BiAbs, and one IgGλλ BiAb. A submixture containing two IgGκλ BiAbs (without mAbs) can be isolated via two consecutive affinity chromatography steps using media binding specifically to the kappa and lambda chain (FIG. 3, submixture 4).

If four different light chains are co-expressed, the resulting mixtures are more complex and depend on the proportion of kappa and lambda light chains that are co-expressed. Two examples are described in FIGS. 4 and 5 in which two lambda light chains and two kappa light chains or three lambda light chains and one kappa light chain are co-expressed, respectively.

The co-expression of two lambda light chains and two kappa light chain with a common heavy chain generates a mixture (Mixture 1, FIG. 4) that is composed of two IgGλλ mAbs, two IgGκκ mAbs, four IgGκλ BiAbs, one IgGλλ BiAb and one IgGκκ BiAb. All these antibody forms contain and Fc portion and can effectively be purified using for instance Protein A chromatography. As described above, different defined subsets of antibodies can be readily isolated from this initial Mixture 1 using affinity chromatography media binding specifically either to the kappa or lambda chain and thus allowing to capture all antibody forms containing at least one kappa or lambda chain, respectively (FIG. 4, submixture 2 and 3, respectively). Submixture 2 will contain two IgGκκ mAbs, four IgGκλ BiAbs and one IgGκκ BiAb. Submixture 3 will contain two IgGλλ mAbs, four IgGκλ BiAbs and one IgGλλ BiAb. Finally, a mixture containing four IgGκλ BiAbs (without mAbs or BiAbs containing only lambda or only kappa chains) can be isolated via two consecutive affinity chromatography steps using media binding specifically to the kappa and lambda chain (FIG. 4, submixture 4).

In the situation in which 3 lambda light chains and one kappa light chain are co-expressed with a common heavy chain, a mixture (Mixture 1, FIG. 5) that is composed of three IgGλλ mAbs, one IgGκκ mAbs, three IgGκλ BiAbs, three IgGλλ BiAb and one IgGκκ BiAb is generated. All these antibody forms contain and Fc portion and can effectively be purified using for instance Protein A chromatography. As described above, different defined subsets of antibodies can be readily isolated from this initial Mixture 1 (FIG. 5) using affinity chromatography media binding specifically either to the kappa or lambda light chain constant domains such as the CaptureSelect Fab Kappa and CaptureSelect Fab Lambda affinity matrices (GE Healthcare) and thus allowing to capture all antibody forms containing at least one kappa or lambda chain, respectively (FIG. 5, submixtures 2 and 3, respectively). Submixture 2 will contain one IgGκκ mAb and three IgGκλ BiAbs. Submixture 3 will contain three IgGλλ mAbs, three IgGκλ BiAbs and three IgGλλ BiAbs. Finally, a submixture containing three IgGκλ BiAbs (without mAbs of BiAbs containing only lambda or only kappa chains) can be isolated via two consecutive affinity chromatography steps using media binding specifically to the kappa and lambda chain (FIG. 5, submixture 4).

The two situations described above highlight that although in each case four light chains are co-expressed, the nature of the chain expressed (i.e., two kappa light chains and two lambda light chains or 3 lambda light chains and one kappa light chain) lead to the generation and purification of very different mixture subsets that can readily and effectively be isolated by applying the method of the invention. These situations represent only selected examples and do not limit the application of the invention to other situations.

It is obvious that the invention can generally be used to isolate subsets of mAbs and/or BiAbs from complex mixtures, based on their respective content of kappa and lambda light chains. In any situation, it is possible, using affinity chromatography media binding specifically to the constant or variable domain of either kappa or lambda antibody light chains, to purify three types of mixture subsets:
  1. All antibody molecules containing at least one kappa light chain, including both mAbs and BiAbs
  2. All antibody molecules containing at least one lambda light chain, including both mAbs and BiAbs
  3. All BiAbs molecules containing one kappa light chain and one lambda light chain The invention can also be further applied to purify antibody subsets of antibody mixtures containing hybrid light chains as described in patent US20140179547. These hybrid chains are composed of either:
  1. A variable kappa domain fused to a constant lambda domain or
  2. A variable lambda domain fused to a constant kappa domain Similarly to full length lambda or kappa light chains, these hybrid molecules can be selectively separated depending of their variable and constant domain composition by using chromatography media binding either to:
  kappa constant domains (such as CaptureSelect™ LC-kappa (Hu) affinity matrix (Life Technologies, Zug, Switzerland)
  some kappa variable domains (such as Protein L)
  lambda constant domains (such as CaptureSelect™ LC-lambda (Hu) affinity matrix (Life Technologies, Zug, Switzerland)

Figure 6:
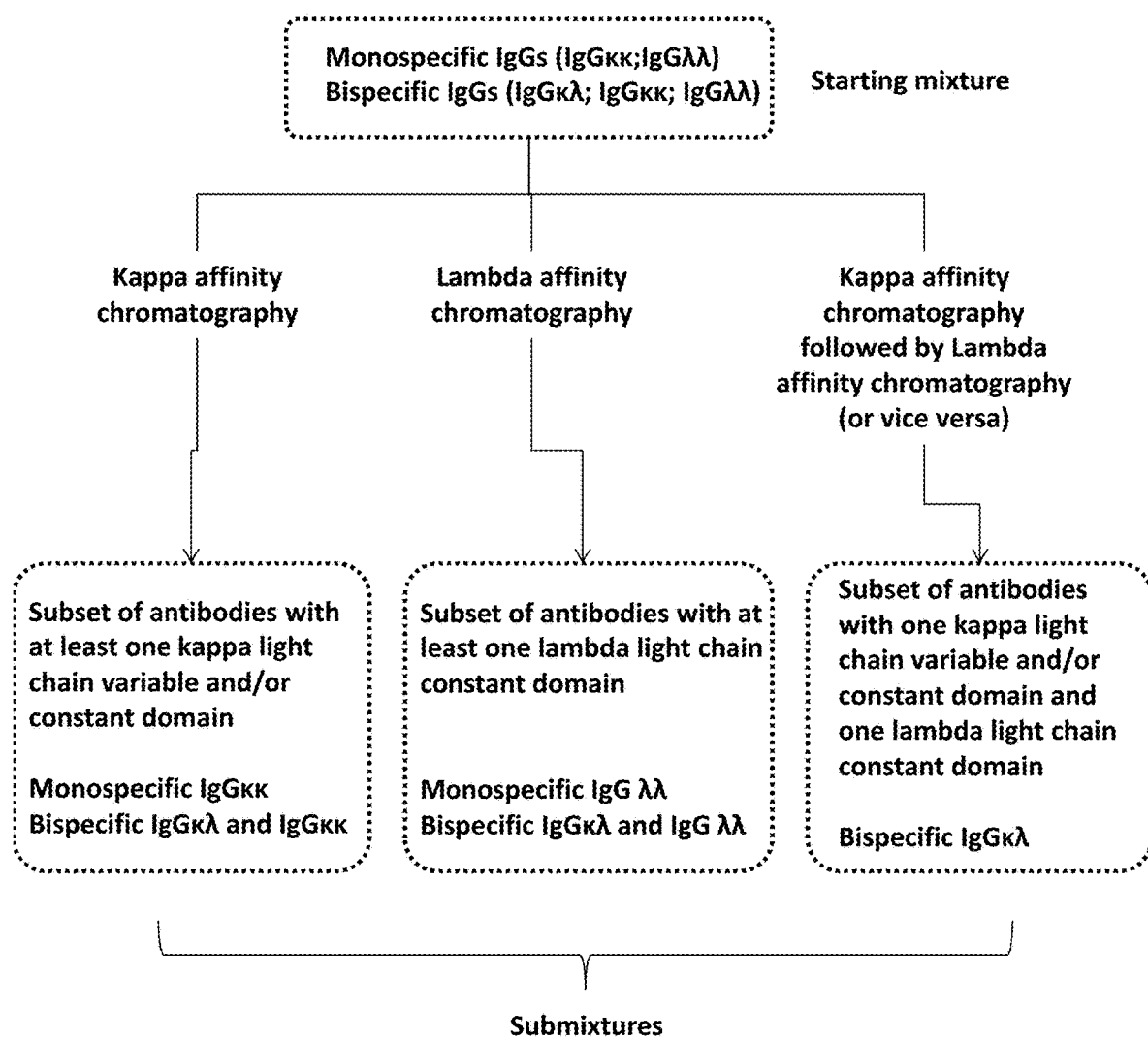
FIG. 6 is a general schematic representation of methods of the disclosure.

The general application of the invention is described in FIG. 6.

The multispecific antibody mixtures of the disclosure are useful in a variety of indications. Subsets of antibody mixtures can have multiple applications for the development of therapeutic modalities relying on modes of actions that are not enabled by mAbs, mAb mixtures or BiAbs.

In particular the invention allows for the straightforward generation of fully human BiAb mixtures using a single cell line, which represents a significant advantage. Indeed, as described above the combination of two individual mAbs leads to significant increases in costs. This limitation is obviously even more significant if two individual BiAb have to be combined, as generation BiAb is more complex and costs higher than for standard mAbs. Examples of potentially interesting mixtures of BiAb as well as how these mixtures can be generated using the invention, are described in more detail below.

Figure 7A:
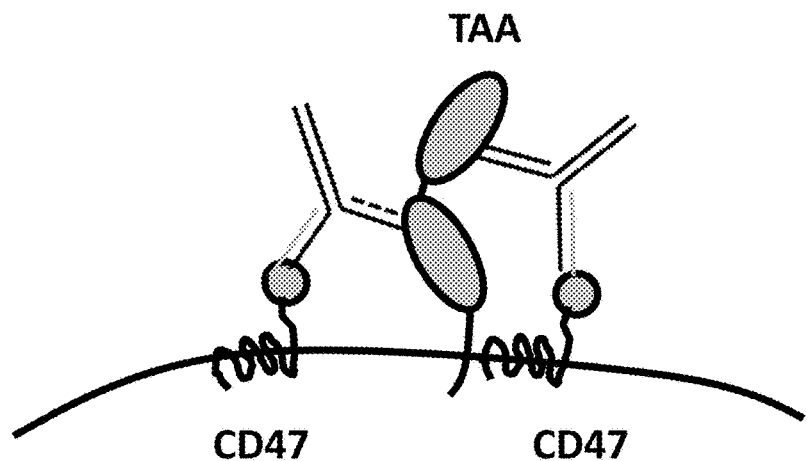
FIG. 7A is a schematic representation of two bispecific antibodies targeting CD47 and two epitopes of a tumor associated antigen (TAA).

Multi-epitope targeting of a tumor associated antigen (TAA) combined with CD47 blockade: CD47 is a ubiquitously expressed receptor that acts as a checkpoint of the innate immune system, repressing phagocytosis via interaction with SIRPα (See e.g., Oldenborg, P. A., CD47: A Cell Surface Glycoprotein Which Regulates Multiple Functions of Hematopoietic Cells in Health and Disease, ISRN Hematol. 2013; 2013:614619; Soto-Pantoja D R, et al., Therapeutic opportunities for targeting the ubiquitous cell surface receptor CD47 (2012), Expert Opin Ther Targets. 2013 January; 17(1):89-103; Sick E, et al., CD47 Update: a multifaced actor in the tumor microenvironment of potential therapeutic interest, Br J Pharmacol. 2012 Decemeber; 167 (7):1415-30). Blockade of CD47 with a BiAb approach avoids toxicities observed with mAbs directed against CD47. A CD47×TAA BiAb allows for restricted inhibition of CD47 only on TAA expressing cells thus avoiding toxicities and poor pharmacokinetic properties. A mixture of two BiAb targeting two epitopes on a single receptor each combining an anti-TAA arm and an anti-CD47 arms would lead to superior anti-CD47 blockade, increased Fc coverage and ultimately better tumor cell killing (FIG. 7A). Indeed, in such a situation, for each TAA molecule, two CD47 receptors can be blocked and two Fc are present at the target cell surface enhancing recruitment of effector cells via Fc gamma receptor interaction.

Co-expression of a common heavy chain along with:
A first lambda light chain driving specificity against a first epitope on a TAA
A second lambda light chain driving specificity against a second epitope on a TAA
A kappa light chain driving specificity against CD47

Figure 7B:
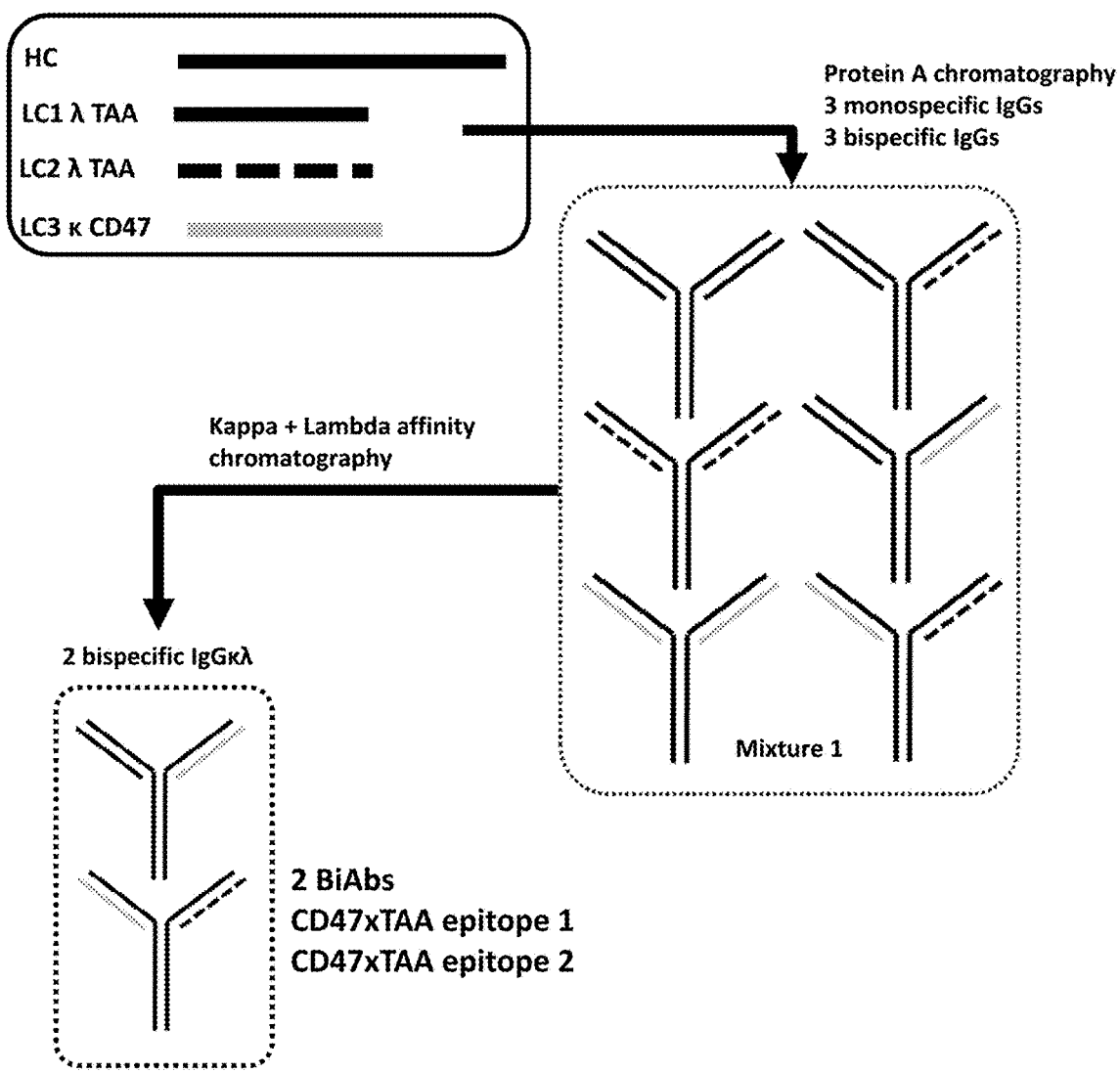
FIG. 7B is a schematic representation of a method of purifying a subset containing two BiAbs (CD47×TAA epitope 1 and CD47×TAA epitope 2) by two step affinity chromatography using kappa-specific affinity media followed by lambda-specific affinity media or vice versa.

From the resulting mixture a subset containing two BiAbs (CD47×TAA epitope 1 and CD47×TAA epitope 2) can be purified by two step affinity chromatography using kappa specific affinity media followed by lambda specific affinity media or vice versa (FIG. 7B).

Figure 8A:
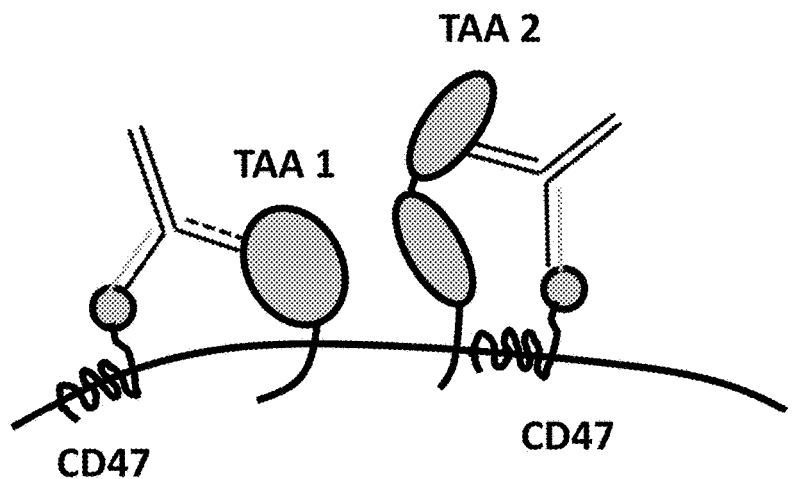
FIG. 8A is a schematic representation of a first bispecific antibody targeting CD47 and a first tumor associated antigen (TAA 1) and a second bispecific antibody targeting CD47 and a second tumor associated antigen (TAA 2).

Multi-TAA targeting combined with CD47 blockade: The example above can be applied to two TAAs expressed by a target cancer cell. A mixture of two BiAb targeting two TAAs, each combining an anti-TAA arm and an anti-CD47 arm would also lead to superior anti-CD47 blockade, increased Fc coverage, further combined with effects linked to the blockade of the TAA and ultimately better tumor cell killing (FIG. 8A).

Co-expression of a common heavy chain along with:
A first lambda light chain driving specificity against a first TAA
A second lambda light chain driving specificity against a second TAA
A kappa light chain driving specificity against CD47

Figure 8B:
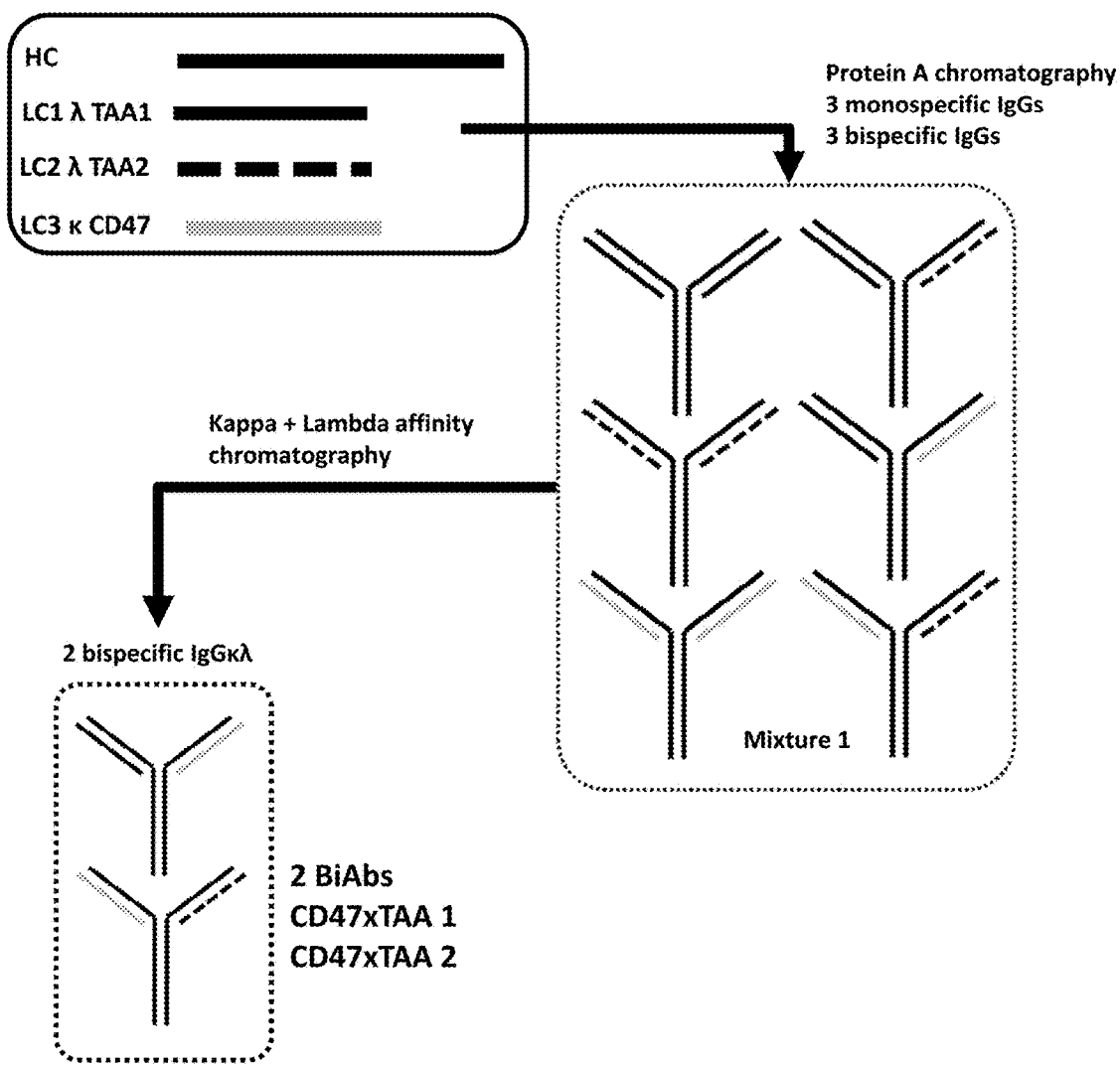
FIG. 8B is a schematic representation of a method of purifying a subset containing two BiAbs (CD47×TAA 1 and CD47×TAA 2) by two step affinity chromatography using kappa-specific affinity media followed by lambda-specific affinity media or vice versa.

From the resulting mixture a subset containing two BiAbs (CD47×TAA 1 and CD47×TAA 2) can be purified by two step affinity chromatography using kappa specific affinity media followed by lambda specific affinity media or vice versa (FIG. 8B).

Figure 9A:
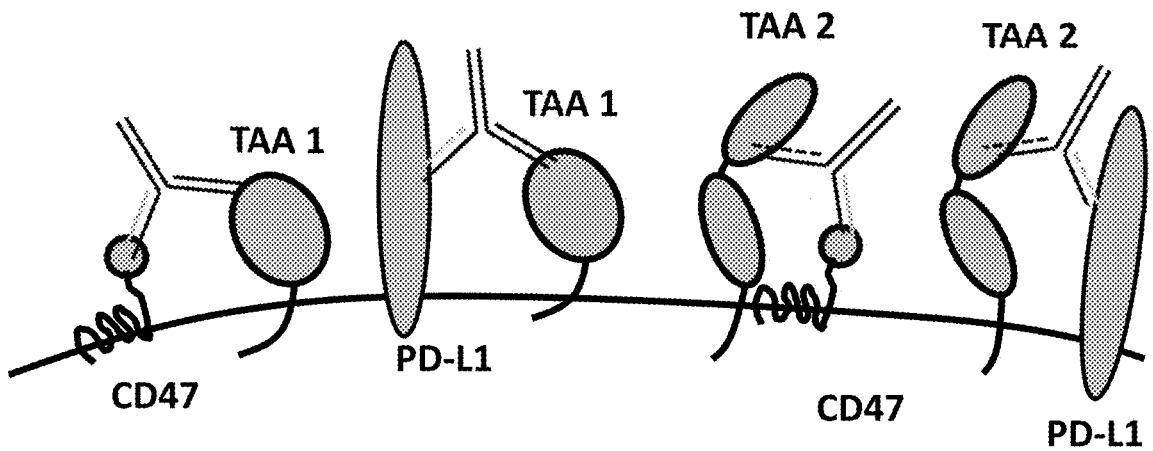
FIG. 9A is a schematic representation of bispecific antibodies targeting multiple tumor associated antigens (TAA 1, TAA 2, et seq.) and/or multiple epitopes on a TAA.

Multi-TAA or epitope targeting combined with blockade of several checkpoint molecules: The approach used in the examples above can be extended to two TAAs (or two epitopes on the same TAA) expressed by a target cancer cell combined with arms blocking two checkpoint receptors, for instance CD47 and PD-L1. Such a mixture would lead to CD47 blockade, PD-L1 blockade, increased Fc coverage, and ultimately better tumor cell killing and potentially durable response of the immune system while avoiding toxicities linked to general monospecific blockade of immune checkpoint (FIG. 9A).

Co-expression of a common heavy chain along with:
A first lambda light chain driving specificity against a first TAA
A second lambda light chain driving specificity against a second TAA
A kappa light chain driving specificity against CD47
A kappa light chain driving specificity against PD-L1

Figure 9B:
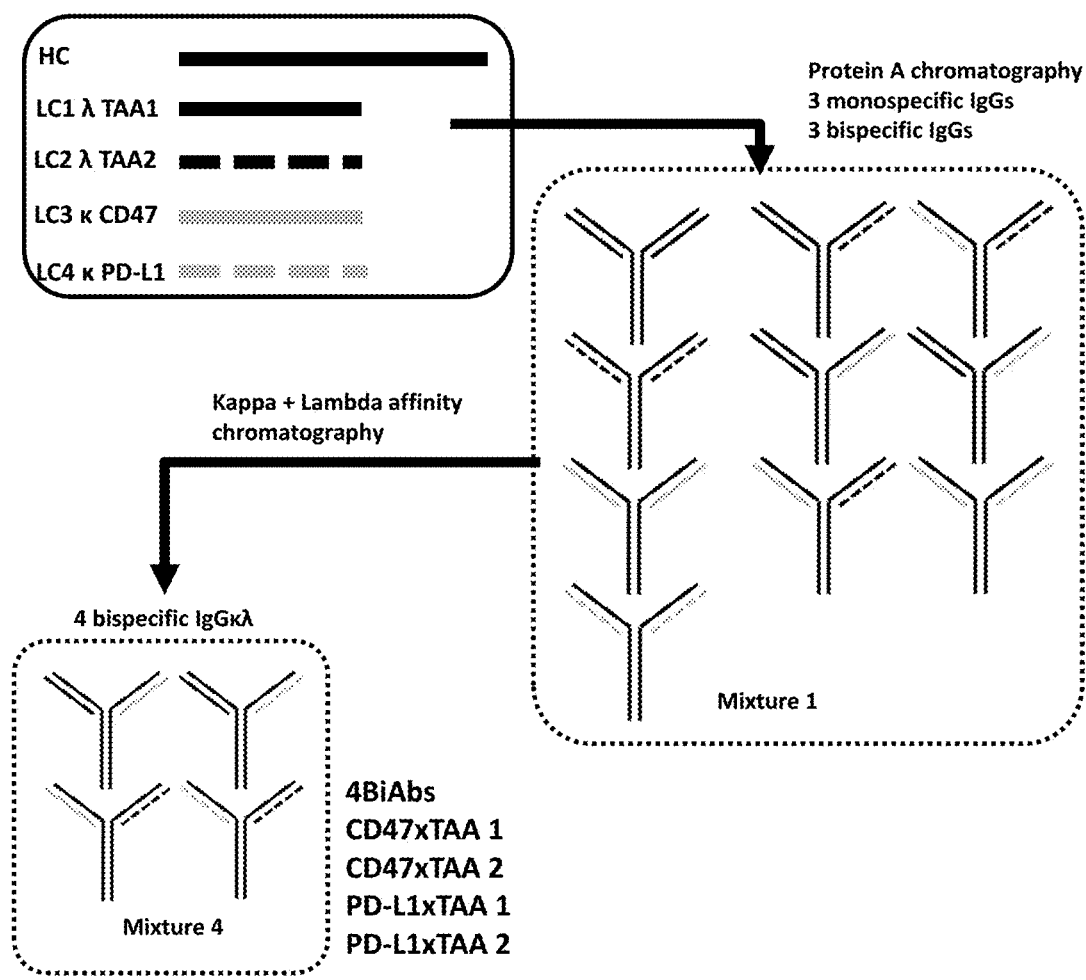
FIG. 9B is a schematic representation of a method of purifying a subset containing 4 different BiAbs (CD47×TAA 1; CD47×TAA 2; PD-L1×TAA 1; PD-L1×TAA 2) by two step affinity chromatography using kappa-specific affinity media followed by lambda-specific affinity media or vice versa.

From the resulting mixture a subset containing 4 different BiAbs (CD47×TAA 1; CD47×TAA 2; PD-L1×TAA 1; PD-L1×TAA 2) can be purified by two step affinity chromatography using kappa specific affinity media followed by lambda specific affinity media or vice versa (FIG. 9B).

Figure 10A:
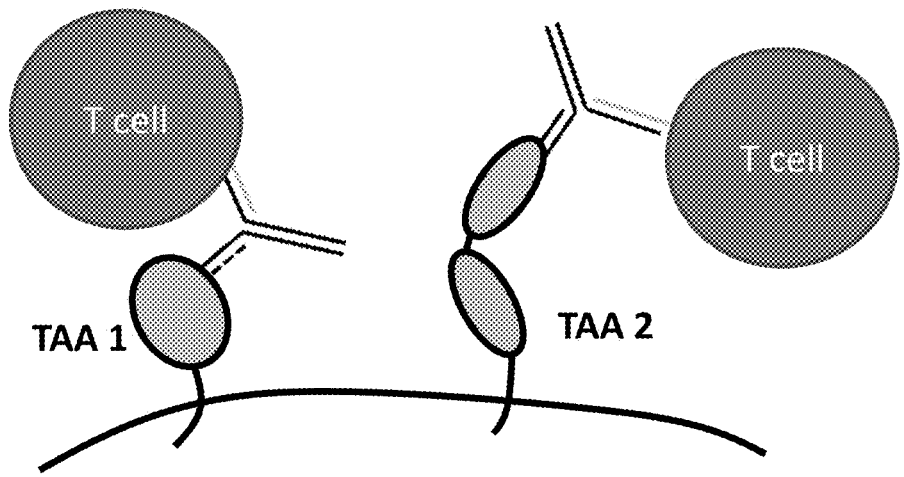
FIG. 10A is a schematic representation of bispecific antibodies for retargeting T cells to multiple tumor associated antigens (TAA 1, TAA 2, et seq.) and/or multiple epitopes on a TAA.

Multi TAA retargeting of T cells: T cell retargeting is a clinically validated and widely pursued approach in oncology (Chames and Baty MAbs. 2009 1(6):539-47). A mixture of BiAb would allow to retarget T cells to two different TAAs (or epitopes on the same TAA) potentially improving treatment efficacy (FIG. 10A).

Co-expression of a common heavy chain along with:
A first lambda light chain driving specificity against a first TAA
A second lambda light chain driving specificity against a second TAA
A kappa light chain driving specificity against CD3

Figure 10B:
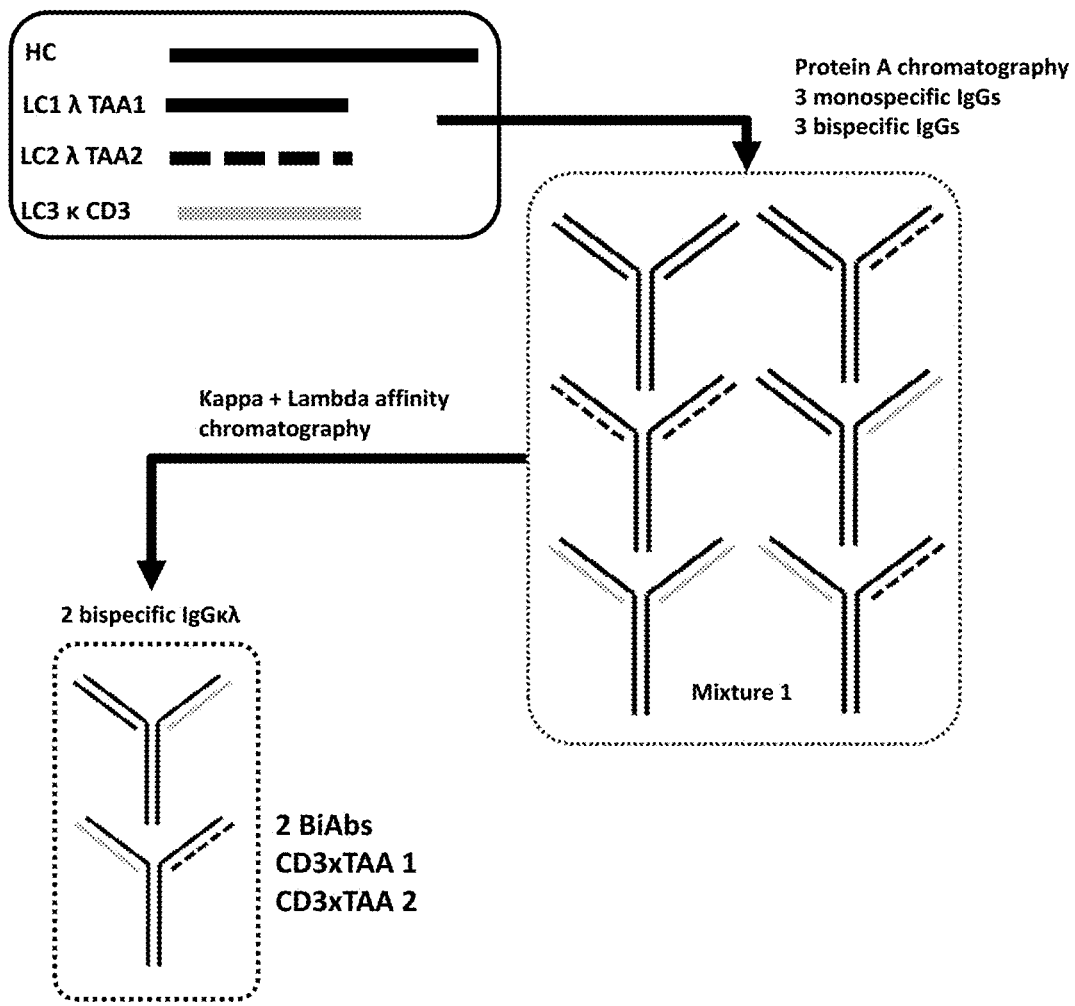
FIG. 10B is a schematic representation of a method of purifying a subset containing 2 different BiAbs (CD3×TAA 1; CD3×TAA 2) by two step affinity chromatography using kappa-specific affinity media followed by lambda-specific affinity media or vice versa.

From the resulting mixture a subset containing 2 different BiAbs (CD3×TAA 1; CD3×TAA 2) can be purified by two step affinity chromatography using kappa specific affinity media followed by lambda specific affinity media or vice versa (FIG. 10B).

The examples above are illustrative and do not limit the possible application that can be pursued by applying the invention. Furthermore is obvious that any kappa chain provided in any example can be replaced by a lambda chain and vice versa.

Another important type application of the invention is the generation of mAb and BiAb mixtures that exclude one or several forms of mAbs. This feature is important as for some targets monospecific, bivalent engagement by a mAb is detrimental and can lead to toxicities and other unwanted effects. For instance it is know that anti-cMet antibodies lead unwanted agonistic activity that have led to the development of monovalent antibodies. Generating a mixture containing anti-cMet antibodies but avoiding the anti c-Met mAb is straightforward using the present invention. As described above targeting of CD47 with a mAb leads to significant toxicities in human. Anti-CD47 mAbs can be removed from mixtures of mAbs targeting other receptors and BiAb targeting CD47 in conjunction with another receptor. Similarly, monoclonal anti-CD3 would also need to be eliminated from anti mixture containing a CD3 binding component.

Figure 11A:
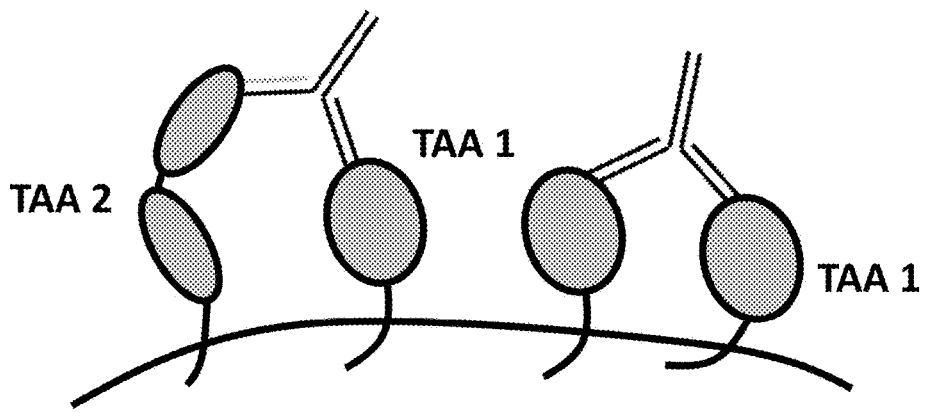
FIG. 11A is a schematic representation of a mixture of a mAb targeting a first TAA, combined with a BiAb targeting the first and a second TAA for which bivalent targeting should be avoided.

Combined monovalent and bivalent targeting of two tumor associated antigens: For instance, a mixture of a mAb targeting a first TAA, combined with a BiAb targeting the first and a second TAA for which bivalent targeting should be avoided. This strategy could be applied for TAAs such as cMet and EGFR (FIG. 11A).

Co-expression of a common heavy chain along with:
A lambda light chain driving specificity against a first TAA 1
A kappa light chain driving specificity against a second TAA 2

Figure 11B:
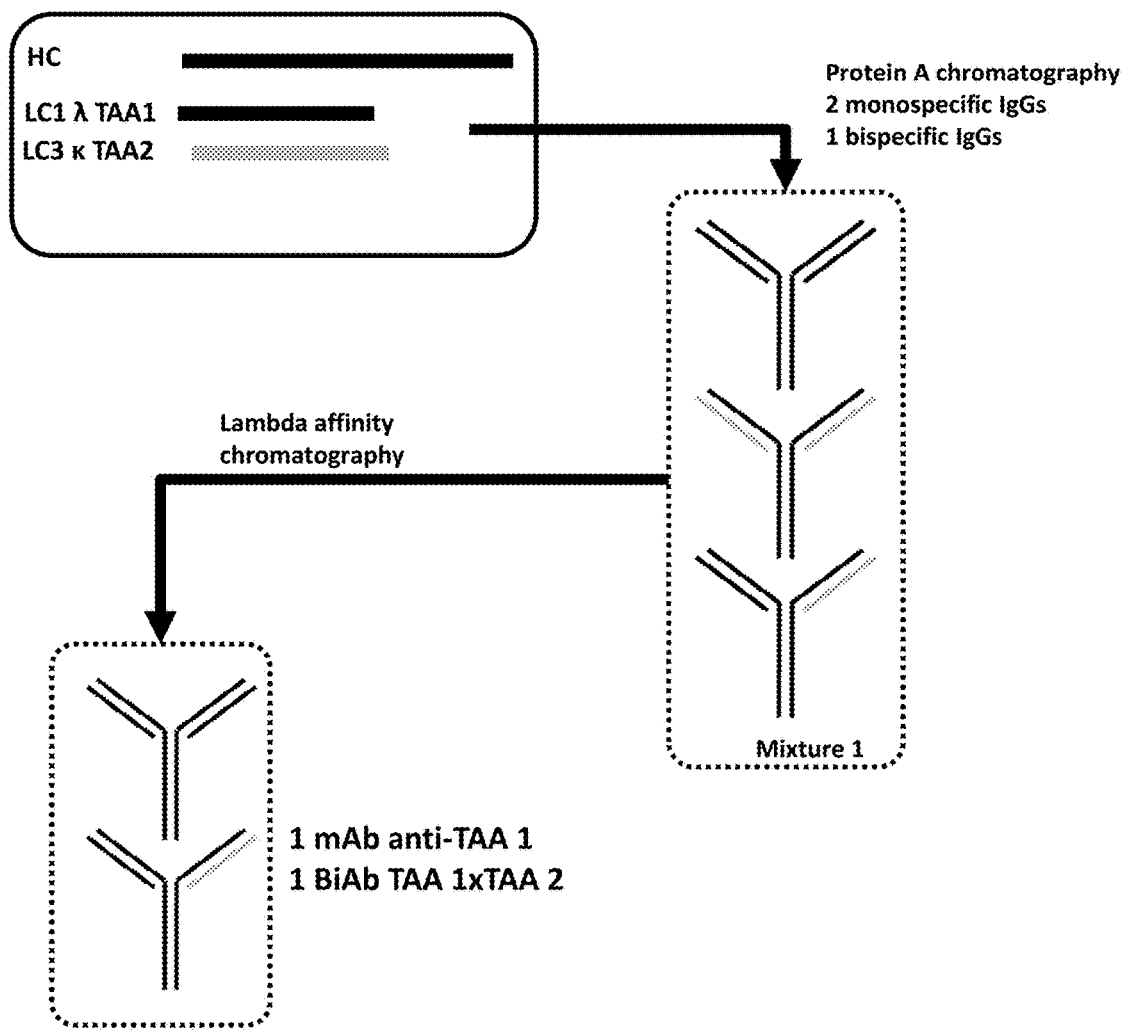
FIG. 11B is a schematic representation of a method of purifying a subset containing a BiAbs (TAA 1×TAA 2) and an anti-TAA1 mAb by two step affinity chromatography using kappa-specific affinity media followed by lambda-specific affinity media or vice versa.

From the resulting mixture a subset containing a BiAbs (TAA 1×TAA 2) and an anti-TAA1 mAb can be purified by affinity chromatography using lambda specific affinity media (FIG. 11B).

Again other applications of subset of antibody mixtures can be rationalized and the examples above do not limit the scope of the invention.

The same principle applies for any antibody isotype as well as antibodies form non-human species provided affinity or other chromatography reagents are available to separate the different submixtures of antibodies.

Furthermore, the same principle of the invention can be applied to F(ab')2 formats in which a single VHCH1 is co-expressed with two or more VκCκ or VλCλ thus leading to the secretion of a mixture of monospecific and bispecific F(ab')2 molecules. These can then be separated into well-defined submixtures according to method of the invention using affinity chromatography media binding to portion of the kappa or lambda light chains. Similarly, hybrid VκCλ and VλCκ can also be used when performing the method of the invention.

EXAMPLES

Example 1

Selection of Antibody Candidates for Bispecific Antibody Generation

Four antibodies targeting different epitopes on hMSLN and an anti-hCD19 antibody, all containing a lambda light chain, as well as an anti-hCD47 antibody containing a kappa light chain were selected for the generation of antibody mixtures. These antibodies all contain the same heavy chain, which are described in PCT Publication No. WO 2014/087248 and in co-pending patent application U.S. Patent Application No. 62/511,669, filed May 26, 2017 and entitled "Anti-CD47×Anti-Mesothelin Antibodies and Methods of Use Thereof", are suitable for the generation of bispecific antibodies based on the κλ body format as described in the Patent Application Publication No. US20140179547. The selected antibodies are listed in Table 3 and the sequences are shown below.

TABLE 3

| Antibody | Specificity | Light chain |
| --- | --- | --- |
| O25 | Anti-hMSLN | Lambda |
| O30 | Anti-hMSLN | Lambda |
| O35 | Anti-hMSLN | Lambda |
| O38 | Anti-hMSLN | Lambda |
| O41 | Anti-hMSLN | Lambda |
| L7-2 | Anti-hCD19 | Lambda |
| K2 | Anti-hCD47 | Kappa |

Each of the anti-hMSLN, anti-hCD19, and anti-hCD47 antibodies in Table 3 includes a common heavy chain (SEQ ID NO: 2) encoded by the nucleic acid sequence shown in SEQ ID NO: 1:

>COMMON-HC-NT
(SEQ ID NO: 1)
GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTTAT

GGTGCTTTTGACTACTGGGGCCAGGGAACCCTGGTCACAGTCTCGAGCGC

CTCCACCAAGGGCCCATCGGTCTTCCCCCTGGCACCCTCCTCCAAGAGCA

CCTCTGGGGGCACAGCGGCCCTGGGCTGCCTGGTCAAGGACTACTTCCCC

GAACCGGTGACAGTCTCGTGGAACTCAGGAGCCCTGACCAGCGGCGTGCA

CACCTTCCCGGCTGTCCTACAGTCCTCAGGACTCTACTCCCTCAGCAGCG

TGGTGACTGTGCCCTCCAGCAGCTTGGGCACCCAGACCTACATCTGCAAC

GTGAATCACAAGCCCAGCAACACCAAGGTGGACAAGAGAGTTGAGCCCAA

ATCTTGTGACAAAACTCACACATGCCCACCGTGCCCAGCACCTGAACTCC

TGGGGGGACCGTCAGTCTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACAACAGCACGTACCGT

GTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAA

CCATCTCCAAAGCCAAAGGGCAGCCCCGAGAACCACAGGTGTATACCCTG

CCCCCATCTCGGGAGGAGATGACCAAGAACCAGGTCAGCCTGACTTGCCT

GGTCAAAGGCTTCTATCCCAGCGACATCGCCGTGGAGTGGGAGAGCAACG

GGCAGCCGGAGAACAACTACAAGACCACGCCTCCCGTGCTGGACTCCGAC

GGCTCCTTCTTCCTCTATAGCAAGCTCACCGTGGACAAGTCCAGGTGGCA

GCAGGGGAACGTCTTCTCATGCTCCGTGATGCATGAGGCTCTGCACAACC

ACTACACGCAGAAGAGCCTCTCCCTGTCTCCGGGTTAA

>COMMON-HC-AA
(SEQ ID NO: 2)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSY

GAFDYWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKRVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG

Each of the anti-hMSLN, anti-hCD19, and anti-hCD47 antibodies in Table 3 includes a common variable heavy domain (SEQ ID NO: 4) encoded by the nucleic acid sequence shown in SEQ ID NO: 3:

>COMMON-VH-NT (SEQ ID NO: 3)
GAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTTAT

GGTGCTTTTGACTACTGGGGCCAGGGAACCCTGGTCACAGTCTCGAGC

>COMMON-VH-AA (SEQ ID NO: 4)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSY

GAFDYWGQGTLVTVSS

The O25 antibody includes a common heavy chain (SEQ ID NO: 2) encoded by the nucleic acid sequence shown in SEQ ID NO: 1 and includes a lambda light chain (SEQ ID NO: 6) encoded by the nucleic acid sequence shown in SEQ ID NO: 5. The variable region of the lambda light chain is bolded in the amino acid sequence below.

>O25-LC-NT (SEQ ID NO: 5)
CAGCCTGTGCTGACTCAGCCGGCTTCCCTCTCTGCATCTCCTGGAGCATC

AGCCAGTCTCACCTGCACCTTGCACAGTGGCATCTCTGTTAAGGATTACA

GGATATACTGGTACCAGCAGAAGCCAGGGCGTCCTCCCCAGTATCTCCTG

AGGTACAAGTCTAATTCAGATATGCAGCAGGGATCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CATGGCCATGGGACTAGTCTTGTGTTCGGCGGAGGGACCAAGCTGACCGT

CCTAGGTCAGCCCAAGGCTGCCCCCTCGGTCACTCTGTTCCCGCCCTCCT

CTGAGGAGCTTCAAGCCAACAAGGCCACACTGGTGTGTCTCATAAGTGAC

TTCTACCCGGGAGCCGTGACAGTGGCTTGGAAAGCAGATAGCAGCCCCGT

CAAGGCGGGAGTGGAGACCACCACACCCTCCAAACAAAGCAACAACAAGT

ACGCGGCCAGCAGCTATCTGAGCCTGACGCCTGAGCAGTGGAAGTCCCAC

AGAAGCTACAGCTGCCAGGTCACGCATGAAGGGAGCACCGTGGAGAAGAC

AGTGGCCCCTACAGAATGTTCATAA

>O25-LC-AA (SEQ ID NO: 6)
QPVLTQPASLSASPGASASLTCTLHSGISVKDYRIYWYQQKPGRPPQYLL

RYKSNSDMQQGSGVPSRFSGSKDASANAGILLISGLQSEDEADYYCMIWH

HGHGTSLVFGGGTKLTVLGQPKAAPSVTLFPPSSEELQANKATLVCLISD

FYPGAVTVAWKADSSPVKAGVETTTPSKQSNNKYAASSYLSLTPEQWKSH

RSYSCQVTHEGSTVEKTVAPTECS

The O25 antibody includes a common variable heavy domain (SEQ ID NO: 4) encoded by the nucleic acid sequence shown in SEQ ID NO: 3 and includes a lambda variable light domain (SEQ ID NO: 8) encoded by the nucleic acid sequence shown in SEQ ID NO: 7.

>O25-VH-NT (SEQ ID NO: 7)
CAGCCTGTGCTGACTCAGCCGGCTTCCCTCTCTGCATCTCCTGGAGCATC

AGCCAGTCTCACCTGCACCTTGCACAGTGGCATCTCTGTTAAGGATTACA

GGATATACTGGTACCAGCAGAAGCCAGGGCGTCCTCCCCAGTATCTCCTG

AGGTACAAGTCTAATTCAGATATGCAGCAGGGATCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CATGGCCATGGGACTAGTCTTGTGTTCGGCGGAGGGACCAAGCTGACCGT

CCTA

>O25-VH-AA (SEQ ID NO: 8)
QPVLTQPASLSASPGASASLTCTLHSGISVKDYRIYWYQQKPGRPPQYLL

RYKSNSDMQQGSGVPSRFSGSKDASANAGILLISGLQSEDEADYYCMIWH

HGHGTSLVFGGGTKLTVL

The O30 antibody includes a common heavy chain (SEQ ID NO: 2) encoded by the nucleic acid sequence shown in SEQ ID NO: 1 and includes a lambda light chain (SEQ ID NO: 10) encoded by the nucleic acid sequence shown in SEQ ID NO: 9. The variable region of the lambda light chain is bolded in the amino acid sequence below.

>O30-LC-NT (SEQ ID NO: 9)
CAGTCTGTGCTGACTCAGCCACCCTCAGCGTCTGGGACCCCCGGGCAGAG

GGTCACCATCTCTTGTTCTGGAAGCAGCTCCAACATCGCGCATGGGCCTG

TAAACTGGTACCAGCAGCTCCCAGGAACGGCCCCCAAACTCCTCATCTAT

GCTACTAATCATCGGCCCTCAGGGGTCCCTGACCGATTTTCTGGCTCCAA

GTCTGGCACCACAGCCTCCCTGACCATCAGTGGGCTCCAGTCTGAGGATG

AGGCTGATTATTACTGTGCTGCATATGATCTTACGGGCTGGTTTGCGTAT

GCTGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>O30-LC-AA (SEQ ID NO: 10)
QSVLTQPPSASGTPGQRVTISCSGSSSNIAHGPVNWYQQLPGTAPKLLIY

ATNHRPSGVPDRFSGSKSGTTASLTISGLQSEDEADYYCAAYDLTGWFAY

AVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS

The O30 antibody includes a common variable heavy domain (SEQ ID NO: 4) encoded by the nucleic acid sequence shown in SEQ ID NO: 3 and includes a lambda variable light domain (SEQ ID NO: 12) encoded by the nucleic acid sequence shown in SEQ ID NO: 11.

\>O30-VL-NT
(SEQ ID NO: 11)
CAGTCTGTGCTGACTCAGCCACCCTCAGCGTCTGGGACCCCCGGGCAGAG

GGTCACCATCTCTTGTTCTGGAAGCAGCTCCAACATCGCGCATGGGCCTG

TAAACTGGTACCAGCAGCTCCCAGGAACGGCCCCCAAACTCCTCATCTAT

GCTACTAATCATCGGCCCTCAGGGGTCCCTGACCGATTTTCTGGCTCCAA

GTCTGGCACCACAGCCTCCCTGACCATCAGTGGGCTCCAGTCTGAGGATG

AGGCTGATTATTACTGTGCTGCATATGATCTTACGGGCTGGTTTGCGTAT

GCTGTGTTCGGCGGAGGGACCAAGCTGACCGTCCTA

\>O30-VL-AA
(SEQ ID NO: 12)
QSVLTQPPSASGTPGQRVTISCSGSSSNIAHGPVNWYQQLPGTAPKLLIY

ATNHRPSGVPDRFSGSKSGTTASLTISGLQSEDEADYYCAAYDLTGWFAY

AVFGGGTKLTVL

The O35 antibody includes a common heavy chain (SEQ ID NO: 2) encoded by the nucleic acid sequence shown in SEQ ID NO: 1 and includes a lambda light chain (SEQ ID NO: 14) encoded by the nucleic acid sequence shown in SEQ ID NO: 13. The variable region of the lambda light chain is bolded in the amino acid sequence below.

\>O35-LC-NT
(SEQ ID NO: 13)
CAGCCTGTGCTGACTCAGCCGGTTTCCCTCTCTGCATCTCCTGGAGCATC

AGTCAGTCTCACCTGCACCTTGCGCAGTGACATCAGGGTTAGAGATTACA

GGATATTCTGGTACCAGCAGAAGCCAGGGAGTCCTCCCCAGTATCTCCTG

AGGTACAAAACCGACTCAGATAAGCAGCAGGGCTCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CGCACCACGGGCACTAGTCTTGTGTTCGGCGGAGGGACCAAGCTGACCGT

CCTAGGTCAGCCCAAGGCTGCCCCCTCGGTCACTCTGTTCCCGCCCTCCT

CTGAGGAGCTTCAAGCCAACAAGGCCACACTGGTGTGTCTCATAAGTGAC

TTCTACCCGGGAGCCGTGACAGTGGCTTGGAAAGCAGATAGCAGCCCCGT

CAAGGCGGGAGTGGAGACCACCACACCCTCCAAACAAAGCAACAACAAGT

ACGCGGCCAGCAGCTATCTGAGCCTGACGCCTGAGCAGTGGAAGTCCCAC

AGAAGCTACAGCTGCCAGGTCACGCATGAAGGGAGCACCGTGGAGAAGAC

AGTGGCCCCTACAGAATGTTCATAA

\>O35-LC-AA
(SEQ ID NO: 14)
QPVLTQPVSLSASPGASVSLTCTLRSDIRVRDYRIFWYQQKPGSPPQYLL

RYKTDSDKQQGSGVPSRFSGSKDASANAGILLISGLQSEDEADYYCMIWH

RTTGTSLVFGGGTKLTVLGQPKAAPSVTLFPPSSEELQANKATLVCLISD

FYPGAVTVAWKADSSPVKAGVETTTPSKQSNNKYAASSYLSLTPEQWKSH

RSYSCQVTHEGSTVEKTVAPTECS

The O35 antibody includes a common variable heavy domain (SEQ ID NO: 4) encoded by the nucleic acid sequence shown in SEQ ID NO: 3 and includes a lambda variable light domain (SEQ ID NO: 16) encoded by the nucleic acid sequence shown in SEQ ID NO: 15.

\>O35-VL-NT
(SEQ ID NO: 15)
CAGCCTGTGCTGACTCAGCCGGTTTCCCTCTCTGCATCTCCTGGAGCATC

AGTCAGTCTCACCTGCACCTTGCGCAGTGACATCAGGGTTAGAGATTACA

GGATATTCTGGTACCAGCAGAAGCCAGGGAGTCCTCCCCAGTATCTCCTG

AGGTACAAAACCGACTCAGATAAGCAGCAGGGCTCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CGCACCACGGGCACTAGTCTTGTGTTCGGCGGAGGGACCAAGCTGACCGT

CCTA

\>O35-VL-AA
(SEQ ID NO: 16)
QPVLTQPVSLSASPGASVSLTCTLRSDIRVRDYRIFWYQQKPGSPPQYLL

RYKTDSDKQQGSGVPSRFSGSKDASANAGILLISGLQSEDEADYYCMIWH

RTTGTSLVFGGGTKLTVL

The O38 antibody includes a common heavy chain (SEQ ID NO: 2) encoded by the nucleic acid sequence shown in SEQ ID NO:1 and includes a lambda light chain (SEQ ID NO: 29) encoded by the nucleic acid sequence shown in SEQ ID NO: 30

\>O38-LC-NT
(SEQ ID NO: 29)
CAGCCTGTGCTGACTCAGCCGGCTTCCCTCTCTGCATCTCCTGGGGCATC

AGCCAGTCTCACCTGCACCTTGCGCAGTGGCATCAACGTTAGAGATTACA

GGATATTCTGGTACCAGCAGAAGCCAGGGAGTCCTCCCCAGTATCTCCTG

AGGTACAAAAGCGCATCAGATAAGCAGCAGGGCTCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CACGATTCGGAGGGGCATGCTTTTGTGTTCGGCGGAGGGACCAAGCTGAC

CGTCCTAGGTCAGCCCAAGGCTGCCCCCTCGGTCACTCTGTTCCCGCCCT

CCTCTGAGGAGCTTCAAGCCAACAAGGCCACACTGGTGTGTCTCATAAGT

GACTTCTACCCGGGAGCCGTGACAGTGGCTTGGAAAGCAGATAGCAGCCC

CGTCAAGGCGGGAGTGGAGACCACCACACCCTCCAAACAAAGCAACAACA

AGTACGCGGCCAGCAGCTATCTGAGCCTGACGCCTGAGCAGTGGAAGTCC

CACAGAAGCTACAGCTGCCAGGTCACGCATGAAGGGAGCACCGTGGAGAA

GACAGTGGCCCCTACAGAATGTTCATAA

\>O38-LC-AA
(SEQ ID NO: 30)
QPVLTQPASLSASPGASASLTCTLRSGINVRDYRIFWYQQKPGSPPQYLL

RYKSASDKQQGSGVPSRFSGSKDASANAGILLISGLQSEDEADYYCMIWH

HDSEGHAFVFGGGTKLTVLGQPKAAPSVTLFPPSSEELQANKATLVCLIS

DFYPGAVTVAWKADSSPVKAGVETTTPSKQSNNKYAASSYLSLTPEQWKS

HRSYSCQVTHEGSTVEKTVAPTECS

The O38 antibody includes a common variable heavy domain (SEQ ID NO: 4) encoded by the nucleic acid sequence shown in SEQ ID NO: 3 and includes a lambda variable light domain (SEQ ID NO: 31) encoded by the nucleic acid sequence shown in SEQ ID NO: 32.

>O38-VL-NT
(SEQ ID NO: 31)
CAGCCTGTGCTGACTCAGCCGGCTTCCCTCTCTGCATCTCCTGGGGCATC

AGCCAGTCTCACCTGCACCTTGCGCAGTGGCATCAACGTTAGAGATTACA

GGATATTCTGGTACCAGCAGAAGCCAGGGAGTCCTCCCCAGTATCTCCTG

AGGTACAAAAGCGCATCAGATAAGCAGCAGGGCTCTGGAGTCCCCAGCCG

CTTCTCTGGGTCCAAAGATGCTTCGGCCAATGCAGGGATTTTACTCATCT

CTGGGCTCCAGTCTGAGGATGAGGCTGACTATTACTGTATGATTTGGCAC

CACGATTCGGAGGGGCATGCTTTTGTGTTCGGCGGAGGGACCAAGCTGAC

CGTCCTA

>O38-VL-AA
(SEQ ID NO: 32)
QPVLTQPASLSASPGASASLTCTLRSGINVRDYRIFWYQQKPGSPPQYLL

RYKSASDKQQGSGVPSRFSGSKDASANAGILLISGLQSEDEADYYCMIWH

HDSEGHAFVFGGGTKLTVL

The O41 antibody includes a common heavy chain (SEQ ID NO: 2) encoded by the nucleic acid sequence shown in SEQ ID NO: 1 and includes a lambda light chain (SEQ ID NO: 18) encoded by the nucleic acid sequence shown in SEQ ID NO: 17. The variable region of the lambda light chain is bolded in the amino acid sequence below.

>O41-LC-NT
(SEQ ID NO: 17)
TCCTATGTGCTGACTCAGCCACCCTCAGTGTCAGTGGCCCCAGGAAAGAC

GGCCAGGATTACCTGTGGGGGAAACAAAATTGGACACCGCGCCGTGCACT

GGTACCAGCAGAAGCCAGGCCAGGCCCCTGTGCTGGTCATCTATTATACC

TATGAGCGGCCCTCAGGGATTCCTGAGCGATTCTCTGGCTCCAACTCTGG

GAACACGGCCACCCTGACCATCAGCAGGGTCGAAGCCGGGGATGAGGCCG

ACTATTACTGTCAGGTGTGGGATTGGTACAGCGAGGGGGGGGTTGTGTTC

GGCGGAGGGACCAAGCTGACCGTCCTAGGTCAGCCCAAGGCTGCCCCCTC

GGTCACTCTGTTCCCGCCCTCCTCTGAGGAGCTTCAAGCCAACAAGGCCA

CACTGGTGTGTCTCATAAGTGACTTCTACCCGGGAGCCGTGACAGTGGCT

TGGAAAGCAGATAGCAGCCCCGTCAAGGCGGGAGTGGAGACCACCACACC

CTCCAAACAAAGCAACAACAAGTACGCGGCCAGCAGCTATCTGAGCCTGA

CGCCTGAGCAGTGGAAGTCCCACAGAAGCTACAGCTGCCAGGTCACGCAT

GAAGGGAGCACCGTGGAGAAGACAGTGGCCCCTACAGAATGTTCATAA

>O41-LC-AA
(SEQ ID NO: 18)
SYVLTQPPSVSVAPGKTARITCGGNKIGHRAVHWYQQKPGQAPVLVIYYT

YERPSGIPERFSGSNSGNTATLTISRVEAGDEADYYCQVWDWYSEGGVVF

GGGTKLTVLGQPKAAPSVTLFPPSSEELQANKATLVCLISDFYPGAVTVA

WKADSSPVKAGVETTTPSKQSNNKYAASSYLSLTPEQWKSHRSYSCQVTH

EGSTVEKTVAPTECS

The O41 antibody includes a common variable heavy domain (SEQ ID NO: 4) encoded by the nucleic acid sequence shown in SEQ ID NO: 3 and includes a lambda variable light domain (SEQ ID NO: 20) encoded by the nucleic acid sequence shown in SEQ ID NO: 19.

>O41-VL-NT
(SEQ ID NO: 19)
TCCTATGTGCTGACTCAGCCACCCTCAGTGTCAGTGGCCCCAGGAAAGAC

GGCCAGGATTACCTGTGGGGGAAACAAAATTGGACACCGCGCCGTGCACT

GGTACCAGCAGAAGCCAGGCCAGGCCCCTGTGCTGGTCATCTATTATACC

TATGAGCGGCCCTCAGGGATTCCTGAGCGATTCTCTGGCTCCAACTCTGG

GAACACGGCCACCCTGACCATCAGCAGGGTCGAAGCCGGGGATGAGGCCG

ACTATTACTGTCAGGTGTGGGATTGGTACAGCGAGGGGGGGGTTGTGTTC

GGCGGAGGGACCAAGCTGACCGTCCTA

>O41-VL-AA
(SEQ ID NO: 20)
SYVLTQPPSVSVAPGKTARITCGGNKIGHRAVHWYQQKPGQAPVLVIYYT

YERPSGIPERFSGSNSGNTATLTISRVEAGDEADYYCQVWDWYSEGGVVF

GGGTKLTVL

The L7-2 antibody includes a common heavy chain (SEQ ID NO: 2) encoded by the nucleic acid sequence shown in SEQ ID NO: 1 and includes a lambda light chain (SEQ ID NO: 22) encoded by the nucleic acid sequence shown in SEQ ID NO: 21.

>L7-2-VL-NT
(SEQ ID NO: 21)
AATTTTATGCTGACTCAGCCCCACTCTGTGTCGGAGTCTCCGGGGAAGAC

GGTAACCATCTCCTGCACCCGCAGCAGTGGCTCTATCGAAGATAAGTATG

TGCAGTGGTACCAGCAGCGCCCGGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACCAGAGCCTGTATGGT

TGGGTGTTCGGCGGAGGGACCAAGCTGACCGTCCTAGGTCAGCCCAAGGC

TGCCCCCTCGGTCACTCTGTTCCCGCCCTCCTCTGAGGAGCTTCAAGCCA

ACAAGGCCACACTGGTGTGTCTCATAAGTGACTTCTACCCGGGAGCCGTG

ACAGTGGCTTGGAAAGCAGATAGCAGCCCCGTCAAGGCGGGAGTGGAGAC

CACCACACCCTCCAAACAAAGCAACAACAAGTACGCGGCCAGCAGCTATC

TGAGCCTGACGCCTGAGCAGTGGAAGTCCCACAGAAGCTACAGCTGCCAG

GTCACGCATGAAGGGAGCACCGTGGAGAAGACAGTGGCCCCTACAGAATG

TTCATAA

>L7-2-LC-AA
(SEQ ID NO: 22)
NFMLTQPHSVSESPGKTVTISCTRSSGSIEDKYVQWYQQRPGSSPTIVIY

YDNERPSGVPDRFSGSIDSSSNSASLTISGLKTEDEADYYCQTYDQSLYG

WVFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSCQ

VTHEGSTVEKTVAPTECS

The L7-2 antibody includes a common variable heavy domain (SEQ ID NO: 4) encoded by the nucleic acid sequence shown in SEQ ID NO: 3 and includes a lambda variable light domain (SEQ ID NO: 24) encoded by the nucleic acid sequence shown in SEQ ID NO: 23.

>L7-2-VL-NT
(SEQ ID NO: 23)
AATTTTATGCTGACTCAGCCCCACTCTGTGTCGGAGTCTCCGGGGAAGAC

GGTAACCATCTCCTGCACCCGCAGCAGTGGCTCTATCGAAGATAAGTATG

TGCAGTGGTACCAGCAGCGCCCGGCAGTTCCCCCACCATTGTGATCTAT

TATGATAACGAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGACCTACGACCAGAGCCTGTATGGT

TGGGTGTTCGGCGGAGGGACCAAGCTGACCGTCCTA

>L7-2-VL-AA
(SEQ ID NO: 24)
NFMLTQPHSVSESPGKTVTISCTRSSGSIEDKYVQWYQQRPGSSPTIVIY

YDNERPSGVPDRFSGSIDSSSNSASLTISGLKTEDEADYYCQTYDQSLYG

WVFGGGTKLTVL

The K2 antibody includes a common heavy chain (SEQ ID NO: 2) encoded by the nucleic acid sequence shown in SEQ ID NO: 1 and includes a kappa light chain (SEQ ID NO: 26) encoded by the nucleic acid sequence shown in SEQ ID NO: 25.

>K2-LC-NT
(SEQ ID NO: 25)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGCGCCCCGAAGACCTTCGGC

CAAGGGACCAAGGTGGAAATCAAACGTACGGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAAGTCTACGCCTGCGAAGTCACCCATCAG

GGCCTGAGCTCGCCCGTCACAAAGAGCTTCAACAGGGGAGAGTGTTAA

>K2-LC-AA
(SEQ ID NO: 26)
DIQMTQSPSSLSASVGDRVTITCRASQSISSYLNWYQQKPGKAPKLLIYA

ASSLQSGVPSRFSGSGSGTDFTLTISSLQPEDFATYYCQQMHPRAPKTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

The K2 antibody includes a common variable heavy domain (SEQ ID NO: 4) encoded by the nucleic acid sequence shown in SEQ ID NO: 3 and includes a kappa variable light domain (SEQ ID NO: 28) encoded by the nucleic acid sequence shown in SEQ ID NO: 27.

>K2-VL-NT
(SEQ ID NO: 27)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGATGCACCCGCGCGCCCCGAAGACCTTCGGC

CAAGGGACCAAGGTGGAAATCAAA

>K2-VL-AA
(SEQ ID NO: 28)
DIQMTQSPSSLSASVGDRVTITCRASQSISSYLNWYQQKPGKAPKLLIYA

ASSLQSGVPSRFSGSGSGTDFTLTISSLQPEDFATYYCQQMHPRAPKTFG

QGTKVEIK

Example 2

Expression and Purification of Bispecific Antibodies Carrying a Lambda and a Kappa Light Chain The simultaneous expression of one heavy chain and two light chains in the same cell can lead to the assembly of three different antibodies. Simultaneous expression can be achieved in different ways such as the transfection of multiple vectors expressing one of the chains to be co-expressed or by using vectors that drive multiple gene expression. A vector pNovikHλ was previously generated to allow for the co-expression of one heavy chain, one Kappa light chain and one Lambda light chain as described in US 2012/0184716 and WO 2012/023053, each of which is hereby incorporated by reference in its entirety. The expression of the three genes is driven by human cytomegalovirus promoters (hCMV), and the vector also contains a glutamine synthetase gene (GS) that enables the selection and establishment of stable cell lines. The VL genes of the anti-hMSLN IgGλ, the anti-hCD19IgGλ or the anti-hCD47 IgGκ were cloned in the vector pNovikHλ, for transient expression in mammalian cells. Peak cells were amplified and split in T175 flasks at a concentration of 8×10⁶ cells per flask in 45 mL culture media containing fetal bovine serum. 30 μg of plasmid DNA were transfected into the cells using Lipofectamine 2000 transfection reagent according to manufacturer's instructions. Antibody concentration in the serum-containing supernatant of transfected cells was measured at several time points during the production using the Bio-Layer Interferometry (BLI) technology. An OctetRED96 instrument and Protein A biosensors were used for quantitation (Pall, Basel, Switzerland). 200 μL of supernatant were used to determine IgG concentration; biosensors were pre-conditioned and regenerated using 10 mM glycine pH 1.7 and IgG calibrators diluted in conditioned PEAK cell medium were prepared for standard curve generation. Concentrations were determined using the dose response 5PL weighted Y standard curve equation and an initial slope binding rate equation. According to antibody concentration, supernatants were harvested 7 to 10 days after transfection and clarified by centrifugation at 1300 g for 10 min. The purification process was composed of three affinity steps. First, the CaptureSelect™ IgG-CH1 affinity matrix (Thermo Fisher Scientific, Waltham, Mass.) was washed with PBS and then added in the clarified supernatant. After incubation overnight at +4° C., supernatants were centrifuged at 1000 g for 10 min, flow through was stored and resin washed twice with PBS. Then, the resin was transferred on spin columns and a solution containing 50 mM glycine at pH 3.0 was used for elution. Several elution fractions were generated, pooled and desalted against 25 mM Histidine/125 mM NaCl pH6.0 buffer using 50 kDaAmicon® Ultra Centrifugal filter units (Merck KGaA, Darmstadt, Germany). The final product, containing total human IgGs from the supernatant, was quantified using a Nanodrop spectrophotometer (NanoDrop Technologies, Wilmington, Del.) and incubated for 30 min at RT and 20 rpm with the appropriate volume of CaptureSelect™ LC-kappa (Hu) affinity matrix (Thermo Fisher Scientific, Waltham, Mass.). Incubation, resin recovery, elution and desalting steps were performed as described previously. The last affinity purification step was performed using the CaptureSelect™ LC-lambda (Hu) affinity matrix (Thermo Fisher Scientific, Waltham, Mass.) applying the same process as for the two previous purifications. The final product was quantified using the Nanodrop. Purified bispecific antibodies were analyzed by electrophoresis in denaturing and reducing conditions. The Agilent 2100 Bioanalyzer was used with the Protein 80 kit as described by the manufacturer (Agilent Technologies, Santa Clara, Calif., USA). 4 µL of purified samples were mixed with sample buffer supplemented with dithiothreitol (DTT; Sigma Aldrich, St. Louis, Mo.). Samples were heated at 95° C. for 5 min and then loaded on the chip. An aliquot from the first purification step (containing the bispecific antibody and both monospecific mAbs) and an aliquot of the final product were loaded on an IsoElectric Focusing (IEF) gel to evaluate the purity of the final purified bispecific antibody (absence of mAb contamination). The aggregate level was determined by SEC-HPLC. Finally, binding of the bispecific antibodies on both targets was assessed using the OctetRED96. Briefly, biotinylated targets (hMSLN, hCD19, hCD47 and an irrelevant target) were loaded on a streptavidin biosensor. Then this biosensor was dipped into a solution containing the bispecific antibody and binding was monitored in real time. All samples were tested for endotoxin contamination using the Limulus Amebocyte Lysate test (LAL; Charles River Laboratories, Wilmington, Mass.). The following bispecific antibodies were expressed an purified:

TABLE 4

| Bispecific antibody | Specificities |
| --- | --- |
| K2O25 | Anti-hCD47; anti-hMSLN |
| K2O30 | Anti-hCD47; anti-hMSLN |
| K2O35 | Anti-hCD47; anti-hMSLN |
| K2O38 | Anti-hCD47; anti-hMSLN |
| K2O41 | Anti-hCD47; anti-hMSLN |
| K2L7-2 | Anti-hCD47; anti-hCD19 |

Example 3

Activity in Phagocytosis Assays of Individual Bispecific Antibodies Targeting hMSLN and hCD47 and Combinations of Bispecific Antibodies Bispecific antibodies targeting a protein or antigen expressed at the surface of a tumor cell and capable of co-engaging CD47 on the same tumor cell can mediate an increase in phagocytic activity of macrophage by preventing the inhibitory signal mediated by the interaction of CD47 with SIRPα. This principle has been described in in PCT Publication No. WO 2014/087248 and in co-pending patent application U.S. Patent Application No. 62/511,669, filed May 26, 2017 and entitled "Anti-CD47×Anti-Mesothelin Antibodies and Methods of Use Thereof". Here we tested the hypothesis of multi-epitope targeting of a tumor associated antigen (TAA), in this case hMSLN combined with CD47 blockade as illustrated in FIG. 7. In order to evaluate the benefit of having a higher density of Fc and higher CD47 blockade per molecule of MSLN, we compared the phagocytic activity mediated by either individual hCD47/hMSLN bispecific antibodies or by pairwise combinations of bispecific antibodies. The hCD47/hCD19 bispecific antibody K2L7-2 was used as a monovalent anti-hCD47 control as no hCD19 is present in the assay. Three tumor cell lines expressing different levels of hCD47 and hMSLN were tested: NCI-N87, HPAC and Caov-3. The levels of cell surface expression of CD47 and Mesothelin for NCI-N87 cells were 43,000 and 27,000, respectively. The levels of cell surface expression of CD47 and Mesothelin for HPAC cells were 105,000 and 13,000, respectively. The levels of cell surface expression of CD47 and Mesothelin for Caov-3 cells were 220,000 and 38,000, respectively.

The assay was performed with human macrophages differentiated from peripheral blood monocytes and NCI-N87, HPAC or CaOV3 as target cells. Macrophages were co-incubated with Calcein AM-labeled target cells (effector: target ratio 1:1) for 2.5 hours at 37° C. in the presence of increasing concentrations of bispecific or monovalent antibody. At the end of the incubation period, supernatants were replaced by complete culture medium. The plates were imaged with the CX5 Imaging platform and 1500 macrophages were acquired and analyzed per conditions. Phagocytosis was evidenced by double-positive events and the phagocytosis indexes were calculated by the software.

Figure 12A:
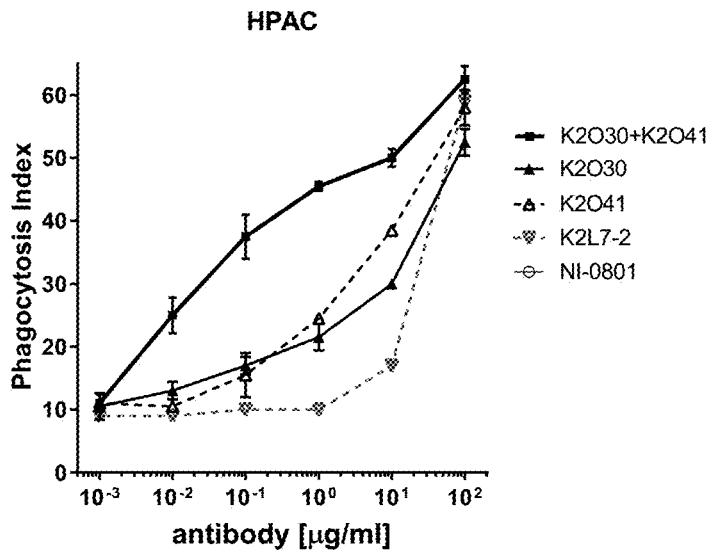
FIGS. 12A, 12B and 12C depict a series of graphs depicting the level of Antibody Dependent Cellular Phagocytosis (ADCP), shown as phagocytosis index, observed in a pancreas adenocarcinoma HPAC cell line in the presence of increasing concentrations of various bispecific antibodies and/or monoclonal antibodies as well as combinations of bispecific antibodies.
Figure 12B:
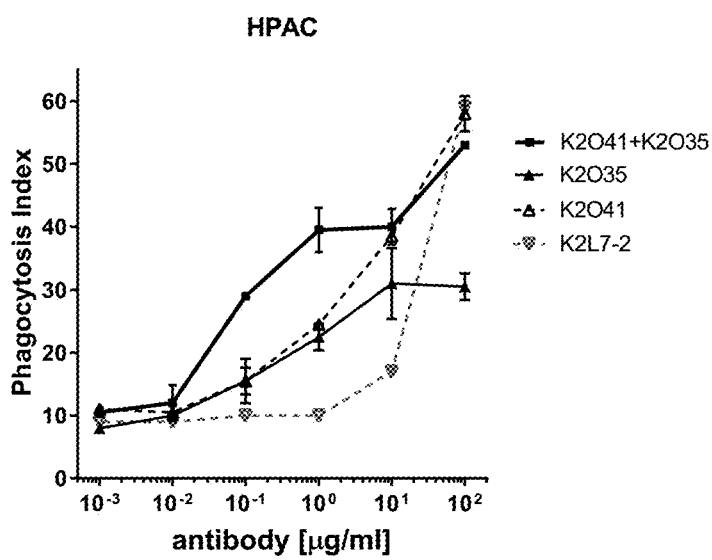
Figure 12C:
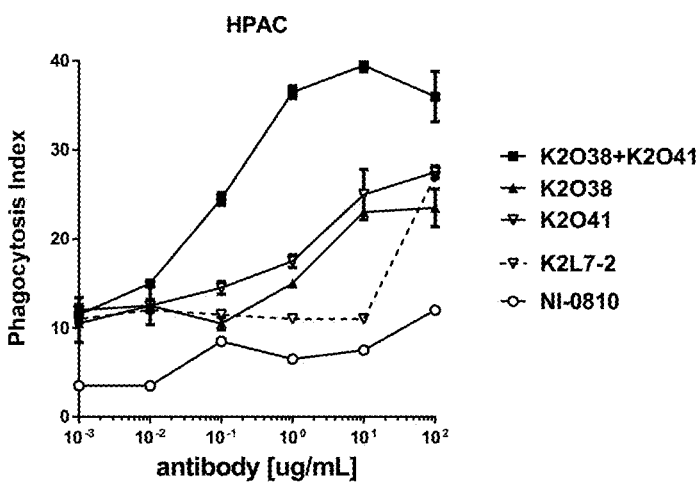
Figure 13A:
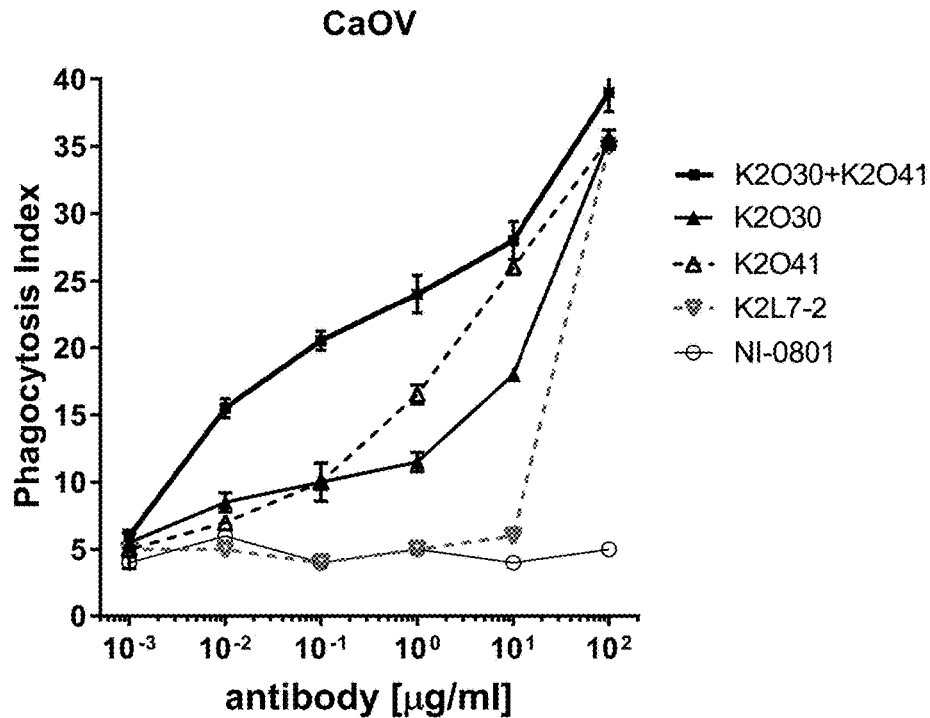
FIGS. 13A and 13B depict a series of graphs depicting the level of ADCP, shown as phagocytosis index, observed in the ovarian adenocarcinoma CaOV cell line in the presence of increasing concentrations of various bispecific antibodies and/or monoclonal antibodies as well as combinations of bispecific antibodies.
Figure 13B:
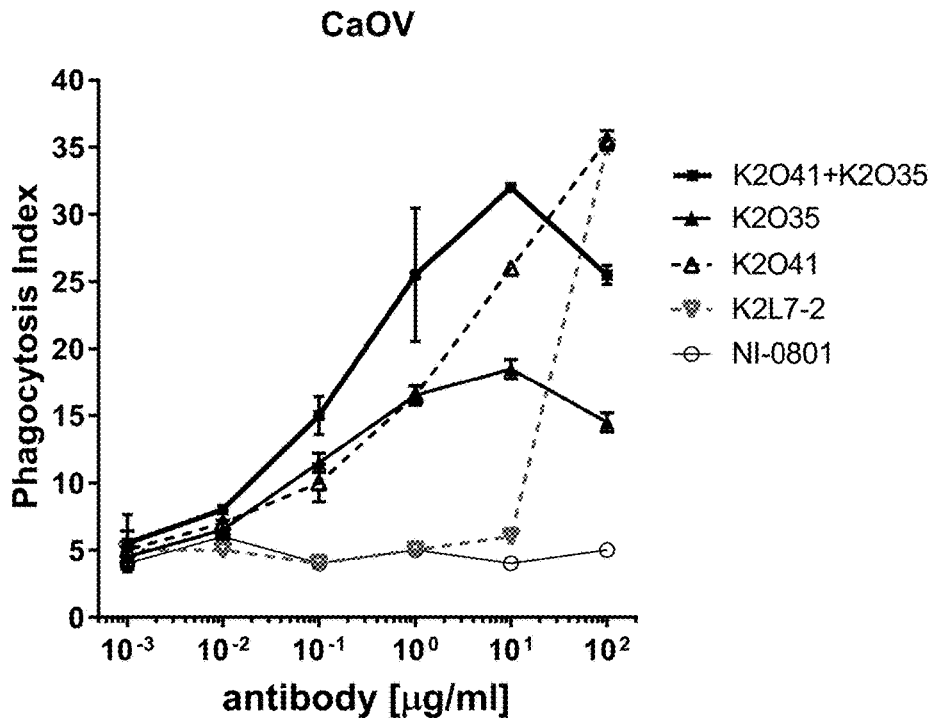
Figure 14A:
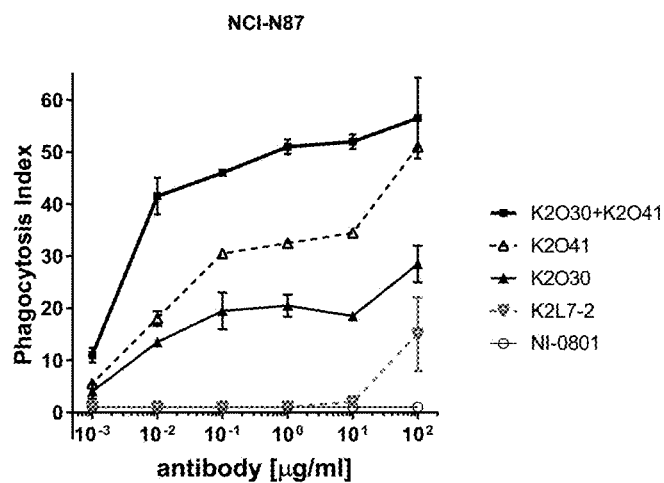
FIGS. 14A, 14B and 14C depict a series of graphs depicting the level of ADCP, shown as phagocytosis index, observed in the gastric carcinoma NCI-N87 cell line in the presence of increasing concentrations of various bispecific antibodies and/or monoclonal antibodies as well as combinations of bispecific antibodies.
Figure 14B:
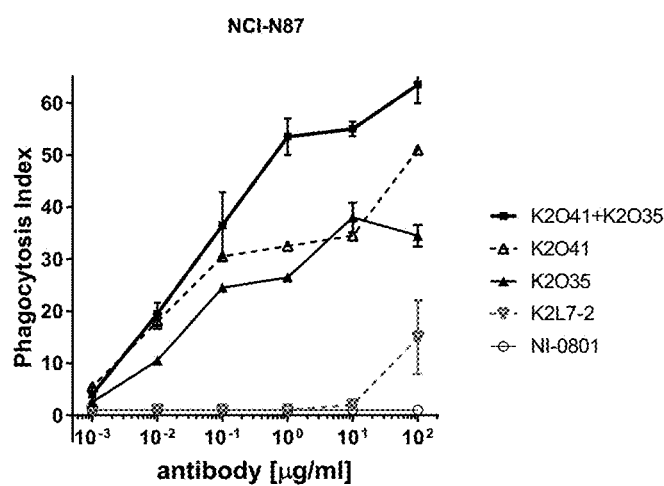
Figure 14C:
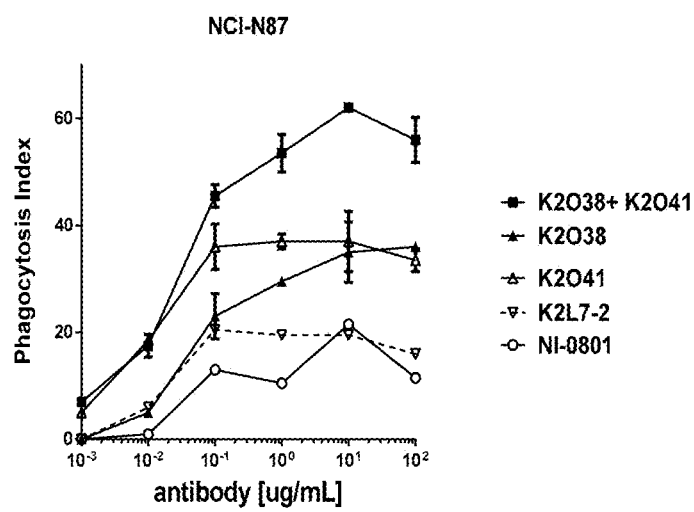
Figure 15:
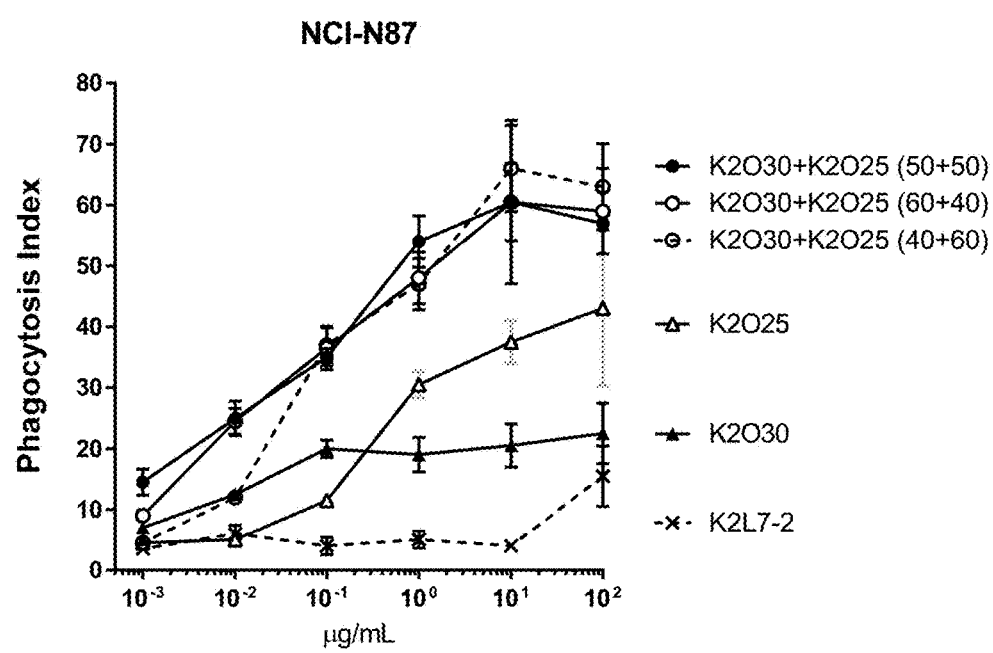
FIG. 15 is a graph depicting the level of ADCP, shown as phagocytosis index, observed in the gastric carcinoma NCI-N87 cell line in the presence of increasing concentrations of various bispecific antibodies as well as combinations using different ratios of bispecific antibodies.

These dose response experiments indicate that the phagocytic activity mediated by the combination of K2O30+K2O41 was superior to the activity of either K2O30 or K2O41 on all three cell types (FIGS. 12A, 13A and 14A). Similarly, the phagocytic activity mediated by the combination of K2O35+K2O41 was superior to the activity of either K2O35 or K2O41 on all there cell types (FIGS. 12B, 13B and 14B). In addition, the phagocytic activity mediated by the combination of K2O38+K2O41 was superior to the activity of either K2O38 or K2O41 on NCI-N87 and HPAC cells (FIGS. 12C and 14C). The combination of K2O30+K2O25 was superior to the activity of either K2O30 or K2O25 on NCI-N87 cells (FIG. 15). In all case the negative control IgG (referred to as NI-0801, described in PCT Publication No. WO2008/106200) or the monovalent anti-hCD47 control only induced minimal or no phagocytic activity. In all these examples, the two bispecific antibodies were added in equal amounts (i.e., at a 50:50 ratio). In order to evaluate whether slight changes in this equimolar ratio would influence the activity, K2O30 and K2O25 were mixed at 40:60 and 60:40 ratios and tested. All ratios gave similar results indicating slight differences in ratio between the two bispecific antibodies do not significantly impact the increase in phagocytic activity of the combination (FIG. 15A).

Example 4

Expression of Four Antibody Chains from a Single Vector

The vector pNovikHλ was modified to enable the expression of an additional light chain. The new vector, pNoviH3L contains four promoters driving the expression of one heavy chain and three light chains. The K2 anti-CD47 Kappa light chain and the two anti-hMSLN Lambda light chains O30 and O25 were cloned into this single vector. All coding sequences and cloning junctions were verified by sequencing. This vector was used in transient transfection as described in Example 2 to verify its functionality, i.e., that bispecific antibodies could be produced. The vector was then linearized for electroporation in Chinese Hamster Ovary (CHO) cells.

Example 5

Expression of Antibody Mixtures Containing Bispecific and Monospecific Antibodies In the studies presented herein, stable CHO lines were transfected and grown using a chemically defined, animal component-free (CDACF) manufacturing process. After transfection by electroporation and selection with MSX, a screening by FACS was performed. The highest producing pools were selected for production in fed batch conditions. Total IgG productivity was assessed for different pools by Octet technology. Affinity purification was performed as described in Example 2. The material after the Protein A chromatography step, thus containing all IgG forms, was analyzed for polypeptide content using an Agilent Bioanalyzer, by isoelectric focusing gel (IEF) and the aggregate level determined by SEC-HPLC. Finally, binding of the bispecific antibodies on both targets was assessed using the OctetRED96. Briefly, biotinylated targets (hMSLN, hCD47 and an irrelevant target) were loaded on a streptavidin biosensor. Then this biosensor was dipped into a solution containing the bispecific antibody and binding was monitored in real time. All samples were tested for endotoxin contamination using the Limulus Amebocyte Lysate test (LAL; Charles River Laboratories, Wilmington, Mass.).

Example 6

Purification of a Submixture Containing Two Bispecific Antibodies

The mixture of all IgG forms (Bispecific and monospecific IgGs) that was expressed and purified in Example 5 was further subjected to two steps of chromatography using media that specifically interact with the Kappa or Lambda light chain constant domains such as the CaptureSelect Fab Kappa and CaptureSelect Fab Lambda affinity matrices (GE Healthcare). These two steps allowed to recover all the IgGs forms containing both a kappa light chain and a lambda light chain as indicated in FIGS. 6 and 7B. The total IgG was then applied to a column containing CaptureSelect Fab kappa affinity matrix (GE Healthcare) equilibrated with ten volumes of PBS. The column was then washed with 5-10 column volumes of PBS. All the immunoglobulin molecules bearing a kappa light chain were eluted from the column by applying 5 column volumes 0.1 M Glycine pH 3.0 and fractions were collected. The fractions containing the antibody were pooled before buffer exchange on an Amicon buffer exchange column (Merck) equilibrated with PBS. The antibody was then applied on a second column containing CaptureSelect Fab lambda affinity matrix equilibrated with ten volumes of PBS. The column was then washed with 5-10 column volumes of PBS. All the immunoglobulin molecules bearing only kappa light chain do bind to the column and were found in the flowthrough. Antibodies carrying a lambda light chain were eluted from the column by applying 5 column volumes 0.1 M Glycine pH 3.0 and fraction were collected. The fractions containing the bispecific antibodies were pooled before buffer exchange on an Amicon buffer exchange column (Merck) equilibrated with PBS. The flow through and elution fraction of each purification step was analyzed by SDS-PAGE and indicated that the antibodies bearing lambda light chains were found in the flow through of the CaptureSelect Fab kappa affinity matrix and, conversely, that antibodies bearing kappa light chains were found in the flow through of the CaptureSelect Fab lambda affinity matrix.

Figure 16A:
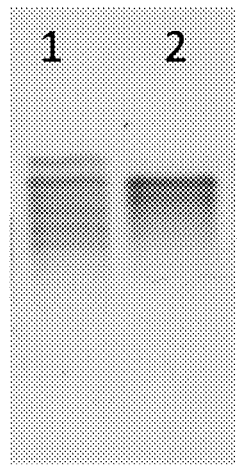
FIG. 16A is a picture of an isoelectric focusing gel on which a sample of the IgG mixture obtained via the co-expression of one heavy chain and three different light chains and purified from the supernatant by Protein A chromatography (lane 1). The K2O25O30 submixture composed of two bispecific antibodies was loaded in lane 2.
Figure 16B:
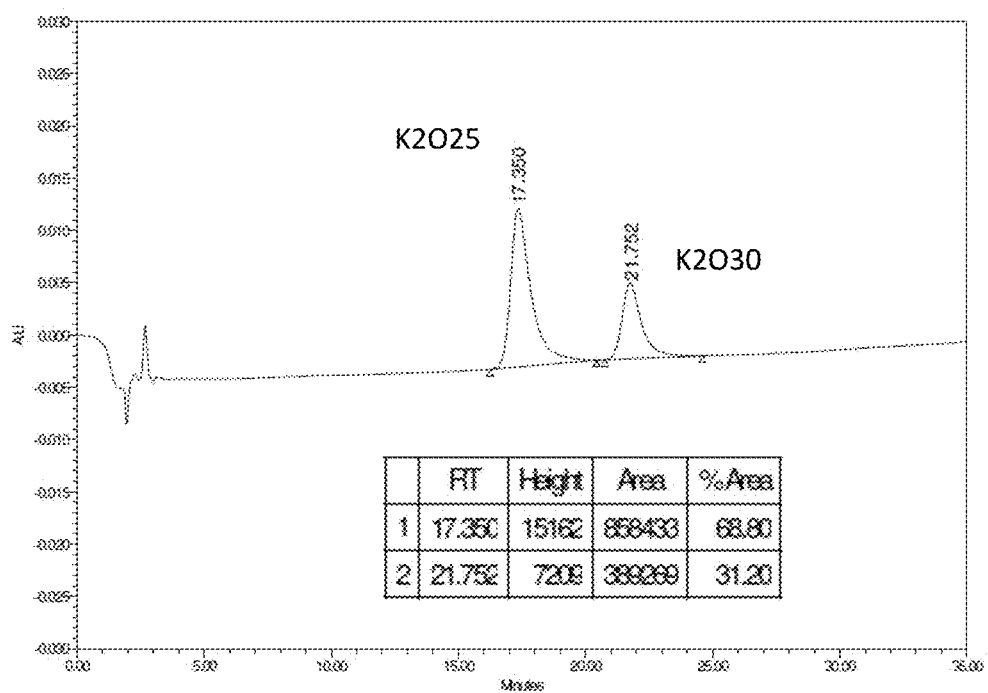
FIG. 16B is a chromatogram obtained after hydrophobic interaction chromatography of the K2O25O30 submixture. Elution time, and peak characteristics are indicated in the inserted table.

The mixture of all IgG forms after obtained after the Protein A step and the K2O25O30 submixture containing two bispecific antibody forms that was purified as described above were analyzed by IEF (FIG. 16A). As expected 6 bands corresponding to the different mono- and bispecific antibody forms were visible for the mixture obtained after Protein A. After the three affinity purification steps, two bands corresponding to the bispecific forms containing a kappa and lambda light chain were visible. The purified K2O25O30 submixture was further analyzed by hydrophobic interaction chromatography (HIC) to determine the relative content of the two bispecific antibody forms. The integration of the two distinct peaks revealed that K2O25O30 contains 69% of K2O25 and 31% of K2O30 (FIG. 16B).

Example 7

Figure 17:
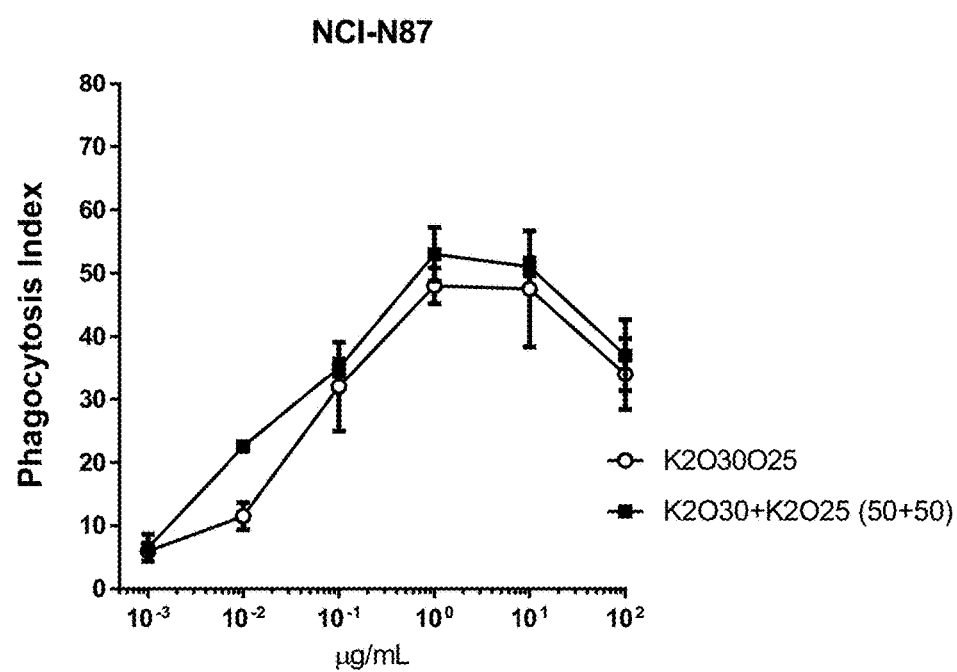
FIG. 17 is a graph depicting the level of ADCP, shown as phagocytosis index, observed in the gastric carcinoma NCI-N87 cell line in the presence of increasing concentrations of the K2O25O30 submixture and an equimolar combination of K2O25 and K2O30.

Activity in Phagocytosis Assays of a Submixture Containing Two Bispecific Antibodies Targeting hMSLN and hCD47 and a Combination of the Same Two Bispecific Antibodies The activity of the K2O25O30 submixture isolated in Example 6 was then compared to the equimolar combination of K2O25 and K2O30 in an in vitro phagocytosis assay using NCI-N87 cells as described in Example 3. The activities of K2O25O30 and the equimolar combination of K2O25 and K2O30 were identical (FIG. 17), indicating that the submixture recapitulates the increase in activity of the combination compared to the activity of the individual bispecific antibodies as described in Example 3.

Example 8

In Vivo Antitumor Activity of Bispecific Antibodies Combinations

The anti-tumor activity of 2 CD47×MSLN κλ bodies (K2O38 and K2O41) and one combinations of CD47× MSLN κλ bodies (K2O38+K2O41) were evaluated in a MSLN-transfected HepG2 model of liver cancer. $3.10^6$ HepG2-MSLN cells were implanted subcutaneously in NOD/SCID mice. Tumor volumes were measured 2 to 3 times per week (using the following formula: (length× $width^2$)/2). Treatment was initiated when the tumor reached between 150 to 200 $mm^3$. Mice were randomized into 8 groups (6-7 mice per group). This experiment compared the effect of combinations of CD47×MSLN KX-bodies to the effect of the CD47×MSLN KX-bodies alone and the MSLN Mab Amatuximab. Antibody was injected i.v. once a week until the end of the experiment (d28). All the antibodies were administered at 60 mg/kg per injection. The tumor volume measurement was used to calculate area under the curve (AUC) for each individual mouse. For statistical analyses, a one-way ANOVA was performed followed by multiple comparison test (Tukey's multiple comparison), using GraphPad Prism. p<0.05 is considered to be statistically significant. Percentage of tumor growth inhibition (TGI), in comparison to isotype control group, was also determined based on tumor volumes, using the formula: % TGI={1-[(Tt-T0)/(Vt-V0)]}×100; with Tt=median tumor volume of treated at time t; T0=median tumor volume of treated at time 0; Vt=median tumor volume of control at time t and V0=median tumor volume of control at time 0.

Figure 18A:
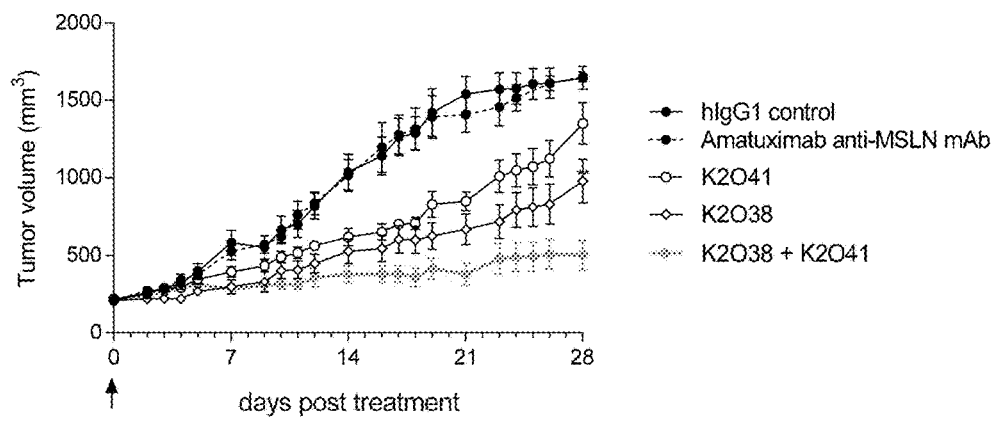
FIG. 18A depicts the anti-tumour activity of 2 CD47×MSLN κλ bodies (K2O38 and K2O41) and their combination (K2O38+K2O41) in a MSLN-transfected HepG2 mouse model of liver cancer.
Figure 18B:
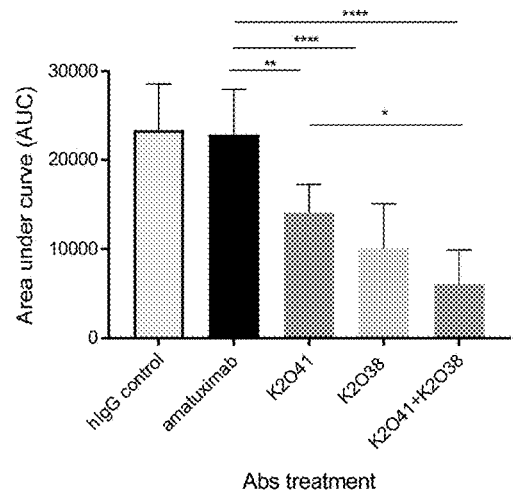
FIG. 18B, shows the areas under the curves and statistical analysis.
Figure 18C:
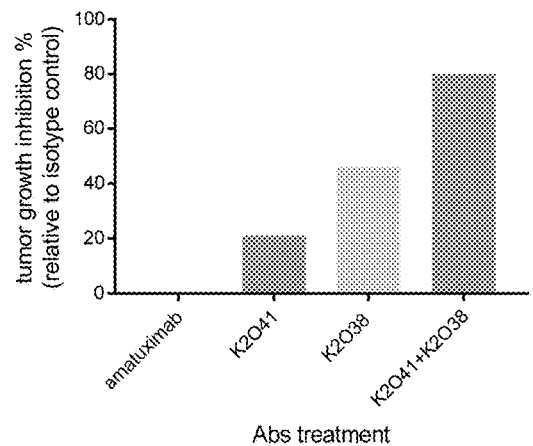
FIG. 18C is a graph showing the tumor growth inhibition observed in the different treatment groups.

As shown in FIG. 18, treatment with the 2 CD47×MSLN κλ bodies significantly reduced tumor growth as compared to hIgG1 control, with a TGI of 21% for K2O41 and 46% for K2O38. The combination demonstrated a superior effect on tumor growth, as compared to the single approach, with a TGI of 80% for K2O41+K2O38. Finally, both the single CD47×MSLN κλ bodies and their combination exhibited a superior anti-tumor effect as compared to Amatuximab, a neutralizing mAb recognizing MSLN, currently under clinical investigation.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of isolating a subset of antibodies:
a. culturing a single cell line capable of expressing:
   i. one immunoglobulin heavy chain; and
   ii. at least three immunoglobulin light chains wherein at least one light chain is a kappa light chain and at least one light chain is a lambda light chain
to produce an antibody mixture of three or more monospecific antibodies and three or more bispecific antibodies;
b. purifying a subset of antibodies from the antibody mixture by at least two affinity chromatography steps, wherein the at least two affinity purification steps include a purification step using a protein A affinity chromatography media followed by:
   i. a kappa constant domain specific affinity chromatography media; or
   ii. a lambda constant specific affinity chromatography media, or
   iii. a combination of the affinity chromatography media of (i) and (ii), wherein the affinity chromatography media of (i) and (ii) are used in any order, thereby isolating a subset of antibodies,
1) wherein when the single cell line expresses:
   a) an immunoglobulin light chain comprising at least a portion of a kappa light chain and two immunoglobulin light chains comprising at least a portion of a lambda light chain; or
   b) an immunoglobulin light chain comprising at least a portion of a lambda light chain and two immunoglobulin light chains comprising at least a portion of a kappa light chain,
the purifying of a subset of antibodies from the antibody mixture is performed using:
   I) kappa constant domain specific affinity chromatography media, wherein the purified subset of antibodies consists of:
      i) one monospecific antibody and two bispecific antibodies; or
      ii) two monospecific antibodies and three bispecific antibodies;
   all comprising at least a portion of a kappa light chain; or
   II) lambda constant domain specific affinity chromatography media, wherein the purified subset of antibodies consists of:
      i) one monospecific antibody and two bispecific antibodies; or
      ii) two monospecific antibodies and three bispecific antibodies; all comprising at least a portion of a lambda light chain; or
   III) kappa constant domain specific affinity chromatography media and lambda constant specific affinity chromatography media, wherein the purified subset of antibodies consists of two bispecific antibodies all comprising at least a portion of a kappa light chain and at least a portion of a lambda light chain; or
2) wherein when the single cell line expresses:
   a) an immunoglobulin light chain comprising at least a portion of a kappa light chain and three immunoglobulin light chains comprising at least a portion of a lambda light chain; or
   b) an immunoglobulin light chain comprising at least a portion of a lambda light chain and three immunoglobulin light chains comprising at least a portion of a kappa light chain; or
   c) two immunoglobulin light chains comprising at least a portion of a kappa light chain and two immunoglobulin light chains comprising at least a portion of a lambda light chain;
the purifying a subset of antibodies is performed using:
   I) kappa constant domain specific affinity chromatography media, wherein the purified subset of antibodies consists of:
      i) one monospecific antibody and three bispecific antibodies; or
      ii) three monospecific antibodies and six bispecific antibodies; or
      iii) two monospecific antibodies and five bispecific antibodies;
   all comprising at least a portion of a kappa light chain; or
   II) lambda constant domain specific affinity chromatography media wherein the purified subset of antibodies consists of:
      i) one monospecific antibody and three bispecific antibodies; or
      ii) three monospecific antibodies and six bispecific antibodies; or
      iii) two monospecific antibodies and five bispecific antibodies;
   all comprising at least a portion of a lambda light chain; or
   III) kappa constant domain specific affinity chromatography media and lambda constant specific affinity chromatography media, wherein the purified subset of antibodies consists of three or four bispecific antibodies all comprising at least a portion of a kappa light chain and at least a portion of a lambda light chain.

2. The method of claim 1, wherein the subset of antibodies comprise both monospecific and bispecific antibodies.

3. The method of claim 1, wherein the subset of antibodies comprises an antibody that binds a different epitope of the same antigen.

* * * * *

UNITED STATES PATENT AND TRADEMARK OFFICE
CERTIFICATE OF CORRECTION

PATENT NO. : 11,401,299 B2
APPLICATION NO. : 16/042889
DATED : August 2, 2022
INVENTOR(S) : Fischer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 251 days.

Signed and Sealed this
Eleventh Day of February, 2025

Coke Morgan Stewart
*Acting Director of the United States Patent and Trademark Office*